(12) United States Patent
Zigelboim et al.

(10) Patent No.: US 12,721,611 B2
(45) Date of Patent: Sep. 1, 2026

(54) CLOSURE DEVICE

(71) Applicant: PYLON MEDICAL LTD., Or Yehuda (IL)

(72) Inventors: Or Zigelboim, Ness Ziona (IL); Niv Avisar, Ramat Gan (IL)

(73) Assignee: PYLON MEDICAL LTD., Or Yehuda (IL)

( * ) Notice: Subject to any disclaimer, the term of this patent is extended or adjusted under 35 U.S.C. 154(b) by 70 days.

(21) Appl. No.: 18/724,874

(22) PCT Filed: Dec. 28, 2022

(86) PCT No.: PCT/IB2022/062826
§ 371 (c)(1),
(2) Date: Jun. 27, 2024

(87) PCT Pub. No.: WO2023/126843
PCT Pub. Date: Jul. 6, 2023

(65) Prior Publication Data

US 2025/0072880 A1 Mar. 6, 2025

Related U.S. Application Data

(60) Provisional application No. 63/295,532, filed on Dec. 31, 2021.

(51) Int. Cl.

| | |
|---|---|
| ***A61B 17/00*** | (2006.01) |
| ***A61B 17/04*** | (2006.01) |
| ***A61B 90/00*** | (2016.01) |

(52) U.S. Cl.
CPC ...... *A61B 17/0057* (2013.01); *A61B 17/0469* (2013.01); *A61B 90/06* (2016.02);
(Continued)

(58) Field of Classification Search
CPC ............ A61B 17/0057; A61B 17/0469; A61B 17/0487; A61B 17/12045; A61B 90/06;
(Continued)

(56) References Cited

U.S. PATENT DOCUMENTS 5,643,293 A 7/1997 Kogasaka et al.
5,830,125 A * 11/1998 Scribner ............ A61B 17/0057 606/139

(Continued)

FOREIGN PATENT DOCUMENTS

WO 1994013211 6/1994
WO WO-9413211 A1 * 6/1994 ......... A61B 17/0469

OTHER PUBLICATIONS

International Search Report and Written Opinion of PCT/IB2022/062826 Completed Mar. 31, 2023; Mailed Jun. 29, 2023 13 Pages.

*Primary Examiner* — Jocelin C Tanner
(74) *Attorney, Agent, or Firm* — The Roy Gross Law Firm, LLC; Roy D. Gross

(57) ABSTRACT

The present invention discloses a closure device having a proximal end and a distal end, introduced into a blood vessel, comprising at least two pre-shaped hollow tubes having a proximal end, substantially at said proximal end of said closure device and a distal end, adapted to be introduced from said distal end of said closure device into said blood vessel; wherein, upon deployment of said two pre-shaped hollow tubes within said blood vessel, said distal ends thereof are adapted to (i) engage into mechanical contact, such that a suture being threaded through at least one of said pre-shaped hollow tube can be extracted from the second pre-shaped hollow tube.

23 Claims, 29 Drawing Sheets

(52) U.S. Cl.
CPC .... *A61B 90/08* (2016.02); *A61B 2017/00022* (2013.01); *A61B 2017/00477* (2013.01); *A61B 2017/00575* (2013.01); *A61B 2017/00623* (2013.01); *A61B 2017/00663* (2013.01); *A61B 2017/00672* (2013.01); *A61B 2090/0807* (2016.02); *A61B 2217/005* (2013.01)

(58) Field of Classification Search
CPC .......... A61B 90/08; A61B 2017/00022; A61B 2017/00477; A61B 2017/00575; A61B 2017/00623; A61B 2017/00663; A61B 2017/00672; A61B 2017/00876; A61B 2017/0472; A61B 2017/06052; A61B 2017/06104; A61B 2090/0807; A61B 2090/3784; A61B 2090/3925; A61B 2217/005
USPC .......................................................... 606/130
See application file for complete search history.

(56) References Cited

U.S. PATENT DOCUMENTS 7,300,444 B1 11/2007 Nielsen et al.
2008/0154286 A1* 6/2008 Abbott .............. A61B 17/0483 606/228

* cited by examiner

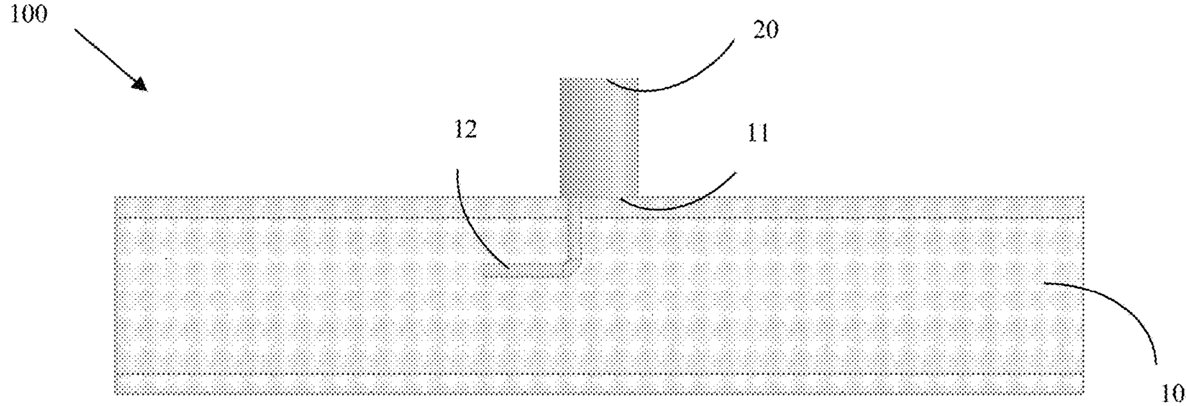
Fig. 1a
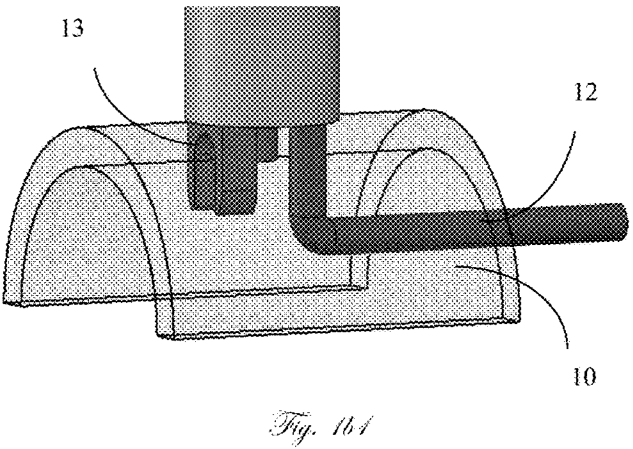
Fig. 1b1

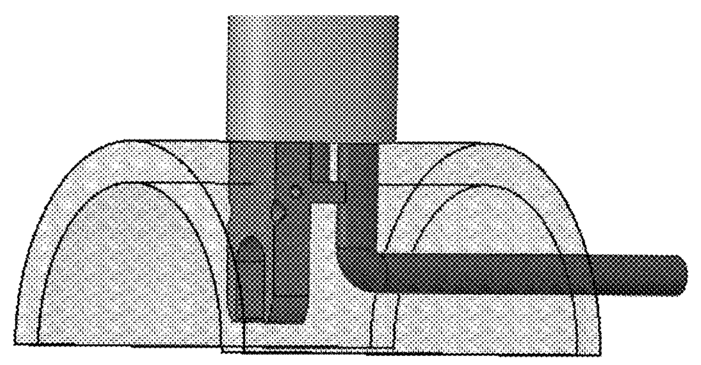
Fig. 1b2
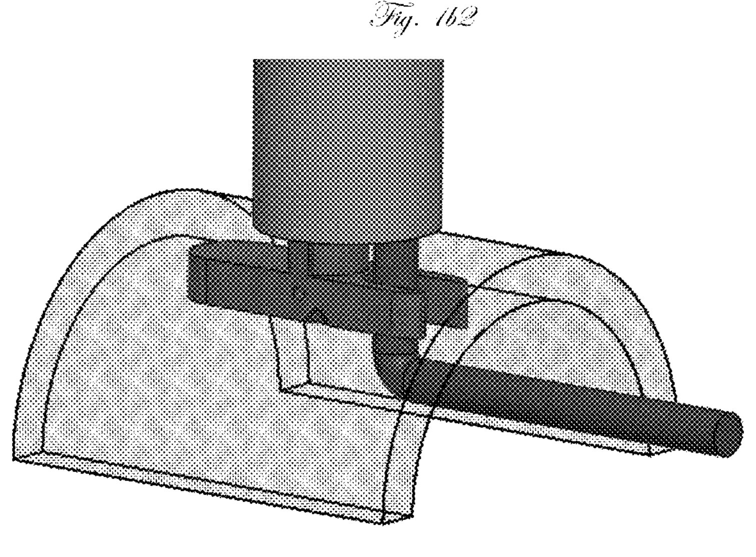
Fig. 1b3

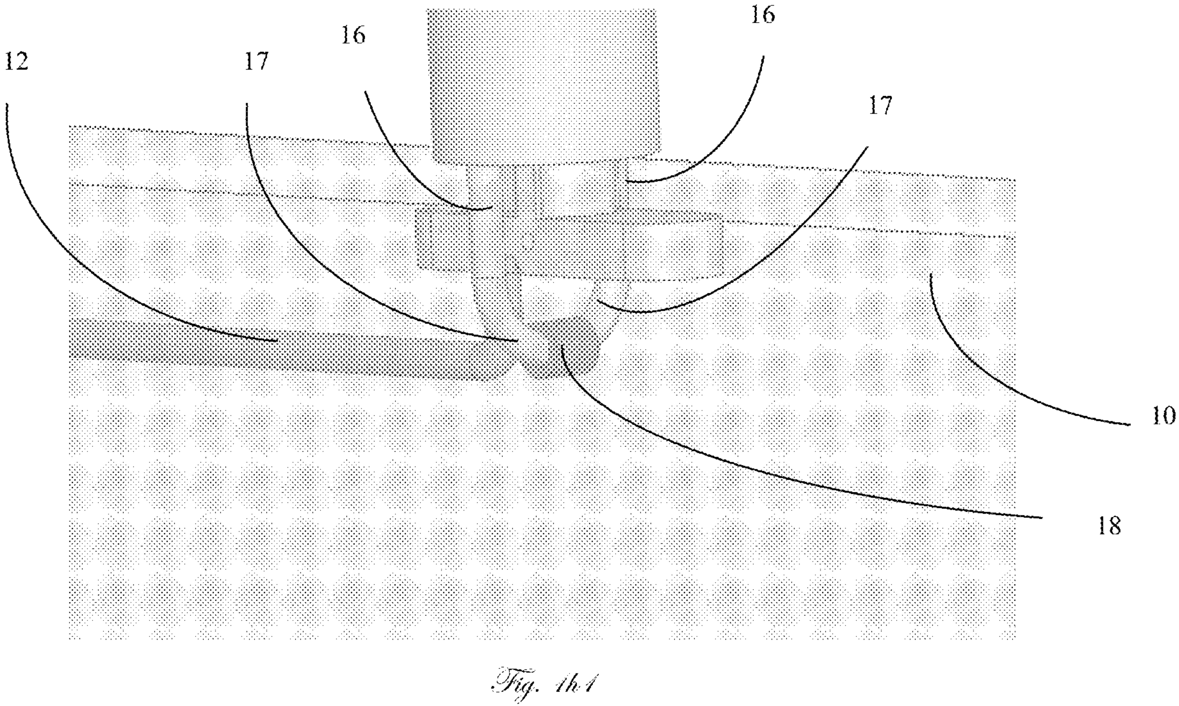
Fig. 1h1

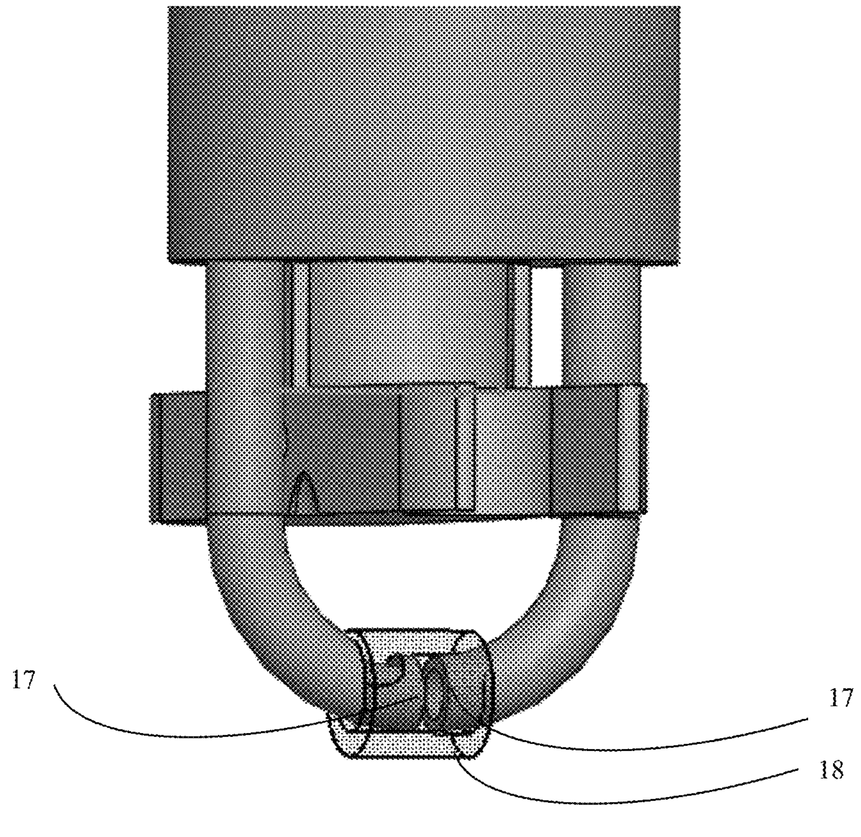
Fig. 1h2

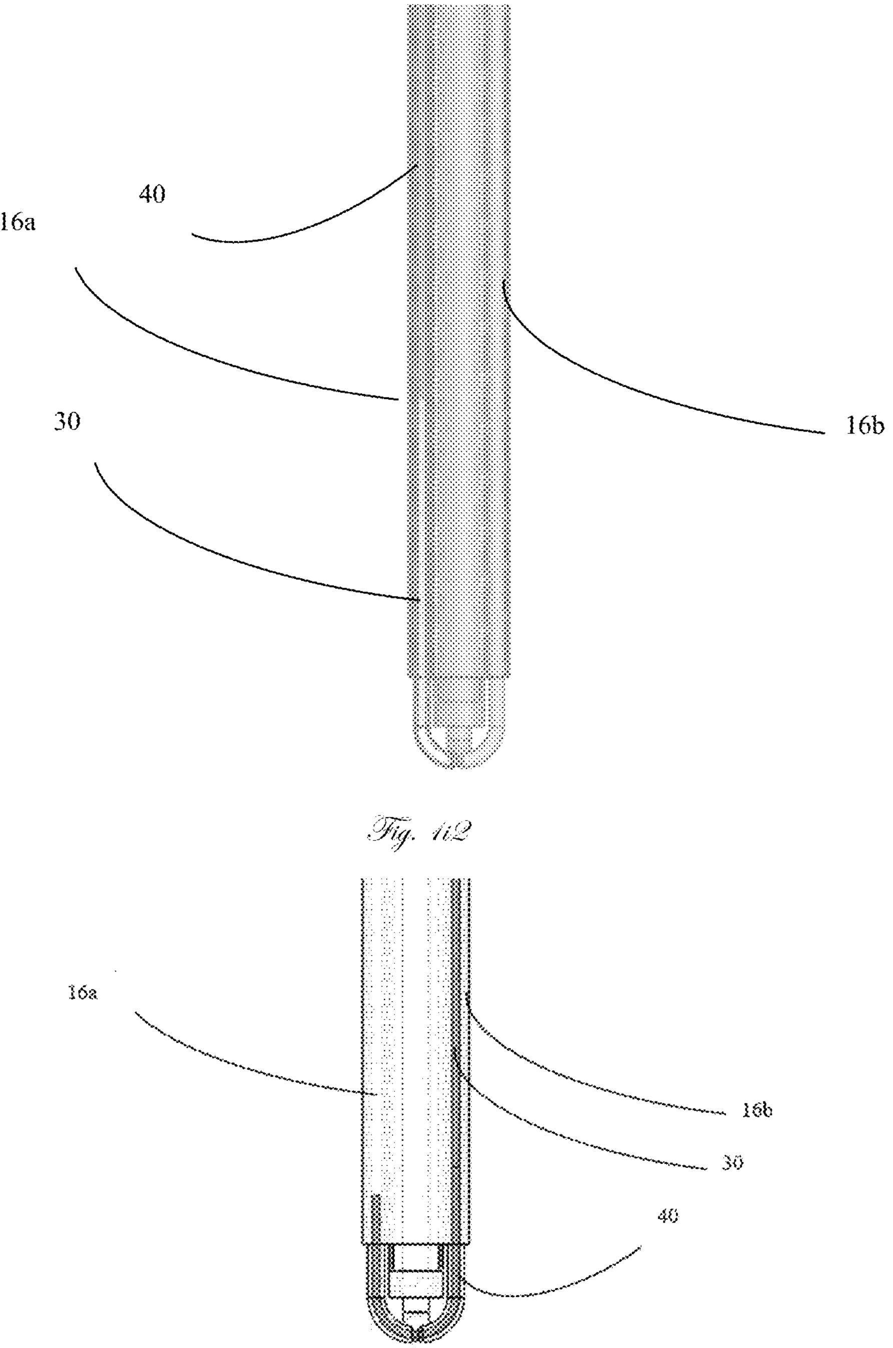
Fig. 1i2
Fig. 1i3

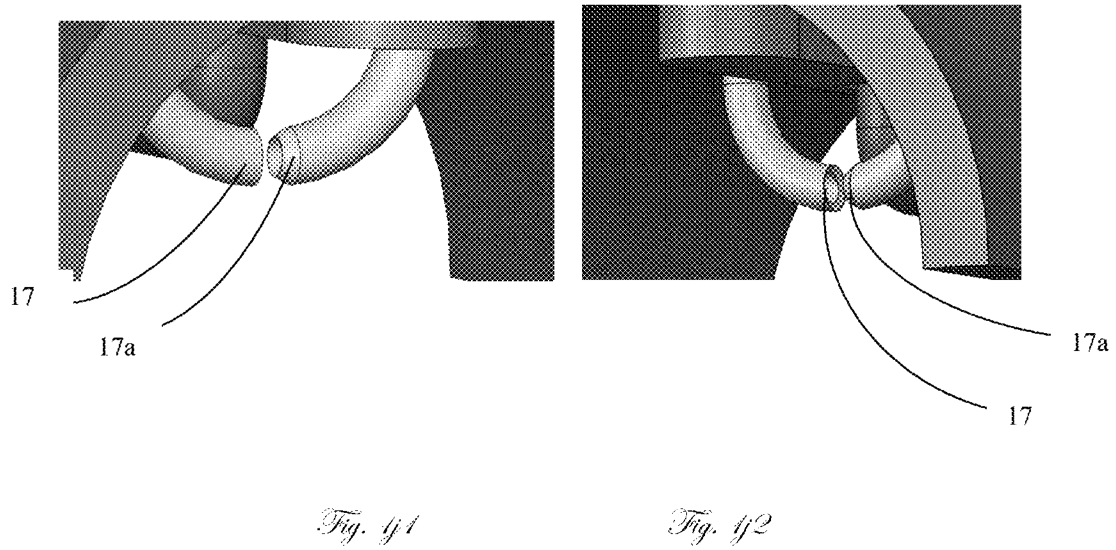
Fig. 9/1
Fig. 9/2

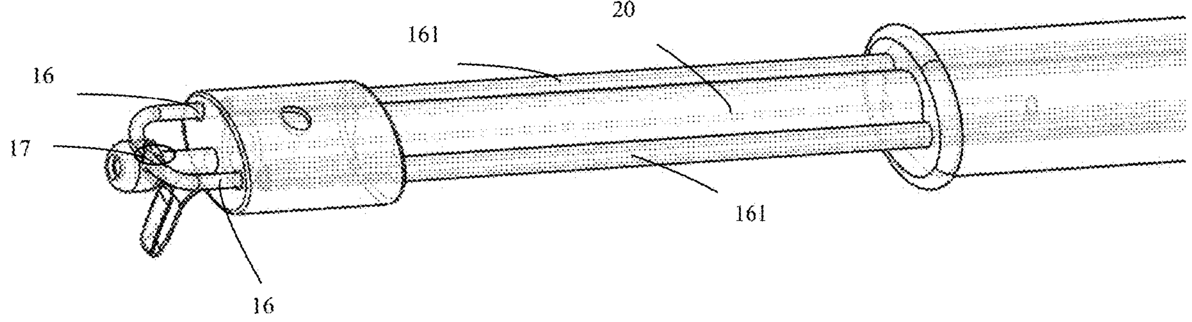
Fig. 4d1
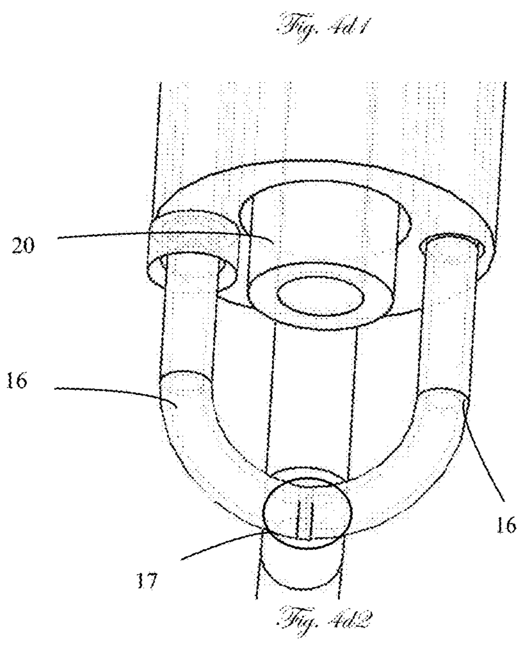
Fig. 4d2

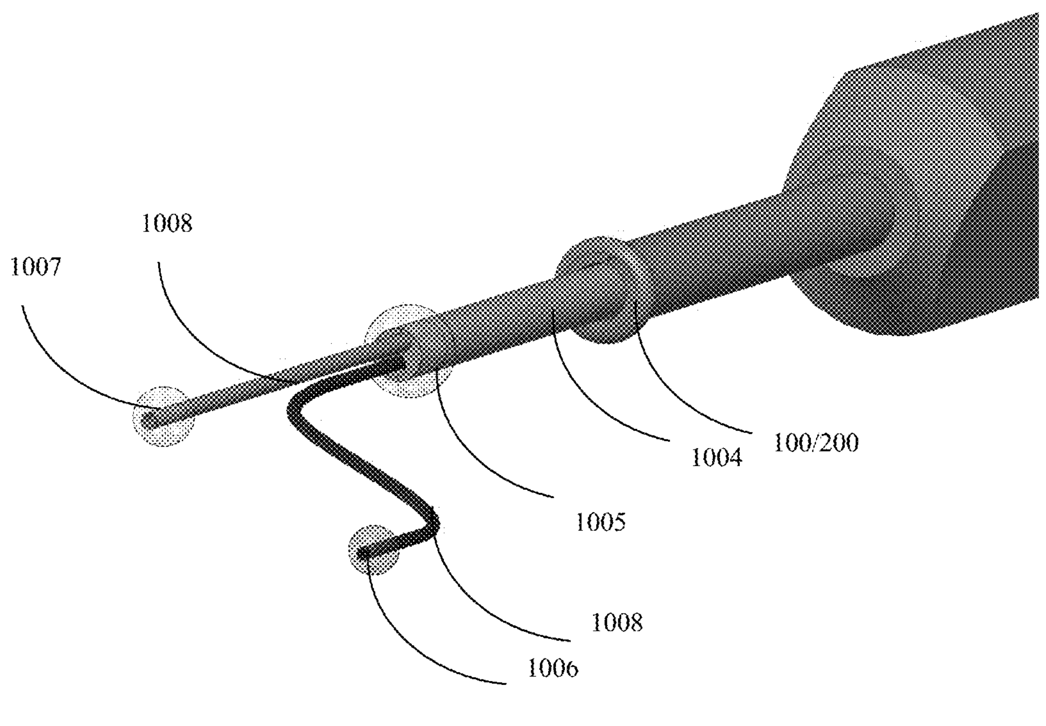
Fig. 6b1
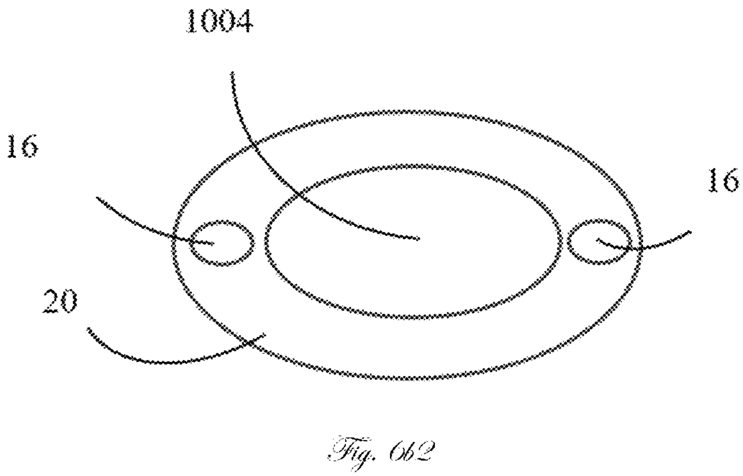
Fig. 6b2

CLOSURE DEVICE

CROSS REFERENCE TO RELATED APPLICATIONS

This application is a National Phase of PCT Patent Application No. PCT/IB2022/062826 having International filing date of Dec. 28, 2022, which claims the benefit of priority of U.S. Provisional Patent Application No. 63/295,532, filed Dec. 31, 2021, the contents of which are all incorporated herein by reference in their entirety.

FIELD OF THE INVENTION

This invention relates to an interventional medical closure device, and to a method of performing an interventional procedure to effect closure of openings in blood vessels (namely arteries and veins). In particular the invention relates to a device which will allow closure of openings within vessel walls, with or without the aid of direct vision (e.g., ultrasound). More specifically, the present invention relates to a carotid intervention and suturing/closure device used during percutaneous trans carotid stenting procedures.

BACKGROUND OF THE INVENTION

The present invention relates to a suture device. Physicians frequently use sutures to close cuts, punctures, incisions and other openings in various biological tissue, such as blood vessels, of the human body. However, unlike other biological tissues, the size and location of suturing blood vessels (e.g., arteries and veins) make suturing thereof even more challenging and difficult.

Recently there has been an increasing number of diagnostic and interventional vascular procedures that are performed translumenally by the percutaneous introduction of instrumentation into a blood vessel. Such procedures require vascular access. Such, vascular access is generally provided through an introducer sheath, which is positioned to extend from outside the patient body into the vascular lumen. They involve accessing a corporeal vessel through the formation of a hole or opening in the vessel wall so that a medical procedure can be performed. After the particular medical procedure has been performed, the access hole in the vessel wall must be closed. A number of prior vascular closure devices and methods have been developed in attempting to provide a solution for the same. Tissue approximation typically involves passing a length of suture into and through adjacent vessel and subcutaneous tissue, across the vessel opening, and back into and through adjacent vessel and subcutaneous tissue. Other closure devices have involved relatively complicated methods and devices for extracting a length of suture from inside the vessel so that the physician can approximate tissue surrounding the hole in the vessel wall through use of the suture.

In many prior art systems, needle deployment is done manually by a physician or operator. Manual deployment involves estimation by the operator of how the needle should be deployed, how fast the trigger for the needle should be actuated, how much force should be applied, etc. The manual method of needles deployment requires the physician to manually pull a lever or button proximally to deploy the needles. The speed or force used to actuate the lever or button will determine the force the needle will have when penetrating the blood vessel. The more force the needle has in penetrating the blood vessel, the greater the possibility of piercing a blood vessel. Thus, the physician must exert sufficient force to penetrate the blood vessel but, on the other hand, he must take care not to exert so much force as to pierce the blood vessel. Manual deployment allows for greater inconsistency and user error as different physicians have differing perception when it comes to how much force or speed to apply when using a device.

A device that address those issues and enables percutaneous surgical site closuring means is still a long-felt need.

One example is a percutaneous transluminal coronary angioplasty (PTCA). A catheter is introduced to the vascular system at a convenient access location and guided through the vascular system to a target location using established techniques. In an arterial catheterization procedure, a relatively small percutaneous incision is made in the femoral or other artery. A catheter is inserted through the incision and directed along an arterial path to a target area.

When vascular access is no longer required, the introducer sheath is removed and bleeding at the puncture site stopped. One common approach for providing hemostasis is to apply external force near and upstream from the puncture site, typically by manual or "digital" compression (it is noted that such is limited to the diameter of the puncture site and also not feasible in the neck). This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis, during which time the patient is uncomfortably immobilized. During this time renewed bleeding may occur, resulting in blood loss through the tract, hematoma and/or pseudoaneurysm formation, as well as arteriovenous fistula formation. Furthermore, patient comfort and physician efficiency are impaired where such external pressure techniques are employed. Moreover, the patient may require immobilization even after the wound is sealed to minimize the risk of wound re-opening.

These complications may require blood transfusion and/or surgical intervention.

Additionally, the risk of hematoma exists while bleeding from the vessel occurs. Such hematoma risk continues until sufficient clotting of the wound site occurs. Moreover, external pressure devices, such as femoral compression systems, are often unsuitable for some patients. Inaccurate skin compression, and thus less effective wound healing, tends to occur as a result.

Furthermore, the incidence of complications from compression-induced hemostasis increases when the size of the introducer sheath grows larger, and/or when the patient is anticoagulated. It is clear that the compression technique for arterial closure can be risky and is expensive and onerous to the patient. Although the risk of complications can be reduced by using highly trained individuals, dedicating such personnel to this task is both expensive and inefficient.

Thus, an adequate closure device is needed where the needles are properly directed through the blood vessel wall at a significant distance from the puncture so that the suture is well anchored in the tissue and can provide tight closure. It is also highly beneficial to ensure that the needle deployment takes place when the device is properly positioned relative to the vessel wall. The ease of deployment and efficacy of the procedure can further be enhanced by reducing the cross-section of that portion of the device, which is inserted into the tissue tract and/or the vessel itself, which may also allow closure of the vessel in a relatively short amount of time without imposing excessive injury to the tissue tract or vessel.

For the above reasons, it would be desirable to provide an improved closure device for suturing vascular punctures.

The present disclosure also relates generally to medical methods and devices for accessing the cerebral arterial vasculature and establishing retrograde blood flow during the interventional treatment of acute ischemic stroke.

Acute ischemic stroke is the sudden blockage of adequate blood flow to a section of the brain, usually caused by thrombus lodging or forming in one of the blood vessels supplying the brain. If this blockage is not quickly resolved, the ischemia may lead to permanent neurologic deficit or even death. The timeframe for effective treatment of stroke is within 3 hours for IV thrombolytic therapy and 6 hours for site-directed intra-arterial thrombolytic therapy or interventional recanalization of a blocked cerebral artery. Even within this time period, there is strong evidence that the shorter the time period between onset of symptoms and treatment, the better the results. Unfortunately, the ability to recognize symptoms, deliver patients to stroke treatment sites, and finally to treat these patients within this timeframe is rare. Despite treatment advances, stroke remains the third leading cause of death in the United States.

Mechanical therapies have involved either capturing and removing clot, dissolving the clot, or disrupting and suctioning the clot. Some use a balloon guide catheter and a microcatheter to deliver a coiled retriever across the clot, and then during balloon occlusion and aspiration of the proximal vessel, pulling the retriever with the clot into the guide catheter. This device has had initially positive results as compared to thrombolytic therapy alone.

Other thrombectomy devices utilize expandable cages, baskets, or snares to capture and retrieve clot. A series of devices using active laser or ultrasound energy to break up the clot have also been utilized. Many of these devices are used in conjunction with aspiration to aid in the removal of the clot and reduce the risk of emboli.

The present invention further discloses a device and method for closing an opening in the carotid arteries post carotid arteries disease treatment.

Furthermore, the present invention discloses interventional catheters such as for carotid artery stenting to treat carotid artery disease.

Carotid artery disease usually consists of deposits of plaque which narrow the internal carotid artery ICA at or near the junction between the common carotid artery and the internal carotid artery. These deposits increase the risk of embolic particles being generated and entering the cerebral vasculature, leading to neurologic consequences such as transient ischemic attacks TIA, ischemic stroke, or death.

Most neurointerventional procedures use a transfemoral access to the carotid to the target cerebral artery. However, this access route is often tortuous and may contain stenosis plaque material in the aortic arch and carotid and brachiocephalic vessel origins, presenting a risk of embolic complications during the access portion of the procedure. In recent years, interventional devices such as wires, guide catheters, stents and balloon catheters, have all been scaled down and been made more flexible to better perform in the neurovascular anatomy.

In carotid artery stenting procedures CAS, embolic protection devices and systems are commonly used to reduce the risk of embolic material from entering the cerebral vasculature. The types of devices include intravascular filters, and reverse flow or static flow systems. Some of the current mechanical clot retrieval procedures use aspiration as a means to reduce the risk of emboli and facilitate the removal of the clot. Lately, a reverse flow protocol having direct surgical access to the common carotid artery CCA (called transcervical or transcarotid access) has been proposed.

The second approach is carotid endarterectomy CEA, an open surgical procedure which relies on clamping the common, internal and external carotid arteries, surgically opening the carotid artery at the site of the disease (usually the carotid bifurcation where the common carotid artery divides into the internal carotid artery and external carotid artery), dissecting away and removing the plaque, and then closing the carotid artery with a suture.

One severe drawback of the current interventions is the amount of time required, post procedure (namely, the post procedure recovery), to suture the artery. Due to the size limitations and the location, suturing is highly challenging. Therefore, there is still a long-felt need for a suturing device that will meet the above-mentioned challenges for used during treatment of the percutaneous trans carotid stenting procedures, including suturing thereof.

SUMMARY OF THE INVENTION

The following describes some examples of embodiments of the invention. Some examples of the invention are described herein and an embodiment may include features from more than one example and/or fewer than all features of an example.

It is one object of the present invention to provide a closure device having a proximal end and a distal end, introduced into a blood vessel, said distal end and said proximal end are interconnected by main sheath, said closure device comprising at least two pre-shaped hollow tubes, each of which having a proximal end, substantially at said proximal end of said closure device; and, a distal end, adapted to be at least partially introduced from said distal end of said closure device into said blood vessel;

further wherein, upon deployment of the distal ends of said two pre-shaped hollow tubes out of said main sheath and into said blood vessel, said distal ends thereof are adapted to engage into mechanical contact therebetween, such that a suture being threaded through at least one of said pre-shaped hollow tube can be extracted from the second pre-shaped hollow tube.

It is another object of the present invention to provide the closure device as defined above, wherein the distal end of each of said pre-shaped hollow tubes is characterized by at least two configurations:

a. a first configuration, in which said pre-shaped hollow tubes are characterized by a shape substantially parallel to said main sheath; and, b. a second configuration, in which said pre-shaped hollow tube is extended and protruding out of the distal end of said closure device, and characterized by having a curved shape.

It is another object of the present invention to provide the closure device as defined above, wherein each of said pre-shaped hollow tubes is convertible from said first configuration to said second configuration by linearly reciprocally moving each of said pre-shaped hollow tubes within said main sheath either towards said proximal end or distal end of said closure device.

It is another object of the present invention to provide the closure device as defined above, wherein said mechanical engagement of said two pre-shaped hollow tubes results in at least one continuous passage between the proximal end of at least one of said two pre-shaped hollow tubes to the proximal end of the second two pre-shaped hollow tubes opening.

It is another object of the present invention to provide the closure device as defined above, wherein said at least one continuous passage configured to automatically guide said suture from the proximal end of at least one of said two pre-shaped hollow tubes to the proximal end of the second two pre-shaped hollow tubes opening, when said suture is inserted and advanced through said at least one continuous passage.

It is another object of the present invention to provide the closure device as defined above, wherein the distal ends of said two pre-shaped hollow tubes, upon deployment out of said closure device and into said blood vessel are substantially aligned, such that a suture being threaded through at least one of said pre-shaped hollow tube can be extracted from the second pre-shaped hollow tube.

It is another object of the present invention to provide the closure device as defined above, wherein said at least two pre-shaped hollow tubes are positioned externally to said main sheath.

It is another object of the present invention to provide the closure device as defined above, wherein said at least two pre-shaped hollow tubes are positioned internally within said main sheath.

It is another object of the present invention to provide the closure device as defined above, wherein said suture is in communication with at least one flexible needle.

It is another object of the present invention to provide the closure device as defined above, wherein at least one of said pre-shaped channels is characterized by a cross sectional area being at least one selected from a group consisting of circular, oval, rectangular, triangular and any combination thereof.

It is another object of the present invention to provide the closure device as defined above, wherein each of said distal ends of said pre-shaped hollow tubes additionally comprising magnetic means.

It is another object of the present invention to provide the closure device as defined above, wherein said magnetic means facilitates said engagement between said distal ends of said two pre-shaped hollow tubes by means of magnetic attraction.

It is another object of the present invention to provide the closure device as defined above, wherein at least one of said distal ends of said pre-shaped hollow tubes is cone-shaped.

It is another object of the present invention to provide the closure device as defined above, wherein said cone-shape facilitates said engagement between said distal ends of said two pre-shaped hollow tubes and ensure alignment therebetween.

It is another object of the present invention to provide the closure device as defined above, wherein at least one of said pre-shaped hollow tubes is characterized by a smaller cross-sectional area than the second pre-shaped hollow tube.

It is another object of the present invention to provide the closure device as defined above, wherein the distal end of said smaller cross-sectional area tube is introduced into the second pre-shaped hollow tube.

It is another object of the present invention to provide the closure device as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is another object of the present invention to provide the closure device as defined above, wherein said suture comprises ratchet mechanism, adapted to be secured on said blood vessel and suture the same.

It is another object of the present invention to provide the closure device as defined above, wherein said suture comprises at least one anchor, adapted to be secured on said blood vessel wall and suture the same.

It is another object of the present invention to provide the closure device as defined above, additionally comprising at least one alignment element adapted to facilitate alignment between said two pre-shaped hollow tubes.

It is another object of the present invention to provide the closure device as defined above, wherein said at least one alignment element comprises at least one arc-shaped groove, adapted to at least partially accommodate the distal end of both said two pre-shaped hollow tubes so as to facilitate alignment between said two pre-shaped hollow tubes.

It is another object of the present invention to provide the closure device as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration and to engage only with the internal surface of said at least one blood vessel.

It is another object of the present invention to provide the closure device as defined above, wherein said at least one foot fixation element is characterized by a blunt edge to prevent any unwanted damage to said at least one blood vessel upon introduction therewithin.

It is another object of the present invention to provide the closure device as defined above, wherein said at least one foot fixation element is adapted to provide counter force to entry of said at least two pre-shaped hollow tubes.

It is another object of the present invention to provide the closure device as defined above, wherein deployment of said pre-shaped hollow tubes is either automatically, manually or semi-automatically/semi-manually provided by at least one handle provided at the proximal end of the device.

It is another object of the present invention to provide the closure device as defined above, wherein said at least one of said at least two pre-shaped hollow tubes are characterized by a rough surface.

It is another object of the present invention to provide the closure device as defined above, wherein the procedure is performed under at least one selected from ultrasound vision, fluoroscopy and any combination thereof.

It is another object of the present invention to provide the closure device as defined above, additionally comprising at least one sensor adapted to at least one selected from a group selected from (a) engagement of said at least two pre-shaped hollow tubes; (b) disengagement of said at least two pre-shaped hollow tubes; (c) any combination thereof.

It is another object of the present invention to provide a method of suturing at least one blood vessel, comprising steps of:

a. obtaining a closure device having a proximal end and a distal end, introduced into a blood vessel, said distal end and said proximal end are interconnected by main sheath, said closure device comprising at least two pre-shaped hollow tubes, each of which having a proximal end, substantially at said proximal end of said closure device and a distal end;
b. at least partially introducing said distal end of said device into said blood vessel;
c. at least partially introducing said two pre-shaped hollow tubes from said distal end of said closure device into said blood vessel thereby at least partially deploying the distal ends of said two pre-shaped hollow tubes out of said main sheath and within said blood vessel;
d. fully deploying said two pre-shaped hollow tubes out of said closure device, within said blood vessel thereby (i) engaging into mechanical contact said distal ends of said two pre-shaped hollow tubes; and, (ii) substantially aligning said distal ends of said two pre-shaped hollow tubes;
e. suturing said blood vessel by at least once threading a suture being through at least one of said pre-shaped hollow tube and extracted the same from the second pre-shaped hollow tube.

It is another object of the present invention to provide the method as defined above, wherein the distal end of each of said pre-shaped hollow tubes is characterized by at least two configurations:

c. a first configuration, in which said pre-shaped hollow tube are characterized by a shape substantially parallel to said main sheath; and,
d. a second configuration, in which said pre-shaped hollow tube is extended and protruding out of the distal end said closure device, and characterized by having a curved shape.

It is another object of the present invention to provide the method as defined above, wherein each of said pre-shaped hollow tubes is convertible from said first configuration to said second configuration by linearly reciprocally moving each of said pre-shaped hollow tubes within said main sheath either towards said proximal end or distal end of said closure device.

It is another object of the present invention to provide the method as defined above, wherein said mechanical engagement of said two pre-shaped hollow tubes results in at least one continuous passage between the proximal end of at least one of said two pre-shaped hollow tubes to the proximal end of the second two pre-shaped hollow tubes opening.

It is another object of the present invention to provide the method as defined above, wherein said at least one continuous passage configured to automatically guide said suture from the proximal end of at least one of said two pre-shaped hollow tubes to the proximal end of the second two pre-shaped hollow tubes opening, when said suture is inserted and advanced through said at least one continuous passage.

It is another object of the present invention to provide the method as defined above, wherein the distal ends of said two pre-shaped hollow tubes, upon deployment out of said closure device and into said blood vessel are substantially aligned, such that a suture being threaded through at least one of said pre-shaped hollow tube can be extracted from the second pre-shaped hollow tube.

It is another object of the present invention to provide the method as defined above, wherein said at least two pre-shaped hollow tubes are positioned externally to said main sheath.

It is another object of the present invention to provide the method as defined above, wherein said at least two pre-shaped hollow tubes are positioned internally within said main sheath.

It is another object of the present invention to provide the method as defined above, wherein at least one of said pre-shaped channels is characterized by a cross sectional area being at least one selected from a group consisting of circular, oval, rectangular, triangular and any combination thereof.

It is another object of the present invention to provide the method as defined above, wherein each of said distal ends of said pre-shaped hollow tubes additionally comprising magnetic means.

It is another object of the present invention to provide the method as defined above, wherein said magnetic means facilitates said engagement between said distal ends of said two pre-shaped hollow tubes by means of magnetic attraction.

It is another object of the present invention to provide the method as defined above, wherein at least one of said distal ends of said pre-shaped hollow tubes is cone-shaped.

It is another object of the present invention to provide the method as defined above, wherein said cone-shape facilitates said engagement between said distal ends of said two pre-shaped hollow tubes and ensure alignment therebetween.

It is another object of the present invention to provide the method as defined above, wherein at least one of said pre-shaped hollow tubes is characterized by a smaller cross-sectional area than the second pre-shaped hollow tube.

It is another object of the present invention to provide the method as defined above, wherein the distal end of said smaller cross-sectional area tube is introduced into the second pre-shaped hollow tube.

It is another object of the present invention to provide the method as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is another object of the present invention to provide the method as defined above, wherein said suture comprises ratchet mechanism, adapted to be secured on said blood vessel and suture the same.

It is another object of the present invention to provide the method as defined above, wherein said suture comprises at least one anchor, adapted to be secured on said blood vessel wall and suture the same.

It is another object of the present invention to provide the method as defined above, additionally comprising at least one alignment element adapted to facilitate alignment between said two pre-shaped hollow tubes.

It is another object of the present invention to provide the method as defined above, wherein said at least one alignment element comprises at least one arc-shaped groove, adapted to at least partially accommodate the distal end of both said two pre-shaped hollow tubes so as to facilitate alignment between said two pre-shaped hollow tubes.

It is another object of the present invention to provide the method as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration and to engage only with the internal surface of said at least one blood vessel.

It is another object of the present invention to provide the method as defined above, wherein said at least one foot fixation element is characterized by a blunt edge to prevent any unwanted damage to said at least one blood vessel upon introduction therewithin.

It is another object of the present invention to provide the method as defined above, wherein said at least one foot fixation element is adapted to provide counter force to entry of said at least two pre-shaped hollow tubes.

It is another object of the present invention to provide the method as defined above, wherein deployment of said pre-shaped hollow tubes is either automatically, manually or semi-automatically/semi-manually provided by at least one handle provided at the proximal end of the device.

It is another object of the present invention to provide the method as defined above, additionally comprising step of disengaging the coupling said two pre-shaped hollow tubes and retracting at least one of which outside said at least one blood vessel.

It is another object of the present invention to provide the method as defined above, wherein said at least one of said at least two pre-shaped hollow tubes are characterized by a rough surface.

It is another object of the present invention to provide the method as defined above, wherein the procedure is performed under at least one selected from ultrasound vision, fluoroscopy and any combination thereof.

It is another object of the present invention to provide the method as defined above, additionally comprising at least one sensor adapted to at least one selected from a group selected from (a) engagement of said at least two pre-shaped hollow tubes; (b) disengagement of said at least two pre-shaped hollow tubes; (c) any combination thereof.

It is another object of the present invention to provide a transcarotid access device, comprising the closure device as defined above.

It is another object of the present invention to provide the transcarotid access device as defined above, additionally comprising at least one reversibly inflatable balloon.

It is another object of the present invention to provide the transcarotid access device as defined above, wherein said at least one additionally reversibly inflatable balloon comprises at least one marker adapted to indicate at least one selected from a group consisting of the location, amount of inflation and any combination thereof of said at least one balloon.

It is another object of the present invention to provide the transcarotid access device as defined above, additionally comprising at least one negative pressure generator, adapted to apply suction within said at least one blood vessel to withdraw fluids from the same.

It is another object of the present invention to provide the transcarotid access device as defined above, wherein the distal end of each of said pre-shaped hollow tubes is characterized by at least two configurations:

a. a first configuration, in which said pre-shaped hollow tube are characterized by a shape substantially parallel to said main sheath; and, b. a second configuration, in which said pre-shaped hollow tube is extended and protruding out of the distal end of said closure device, and characterized by having a curved shape.

It is another object of the present invention to provide the transcarotid access device as defined above, wherein each of said pre-shaped hollow tubes is convertible from said first configuration to said second configuration by linearly reciprocally moving each of said pre-shaped hollow tubes within said main sheath either towards said proximal end or distal end of said closure device.

It is another object of the present invention to provide the transcarotid access device as defined above, wherein said mechanical engagement of said two pre-shaped hollow tubes results in at least one continuous passage between the proximal end of at least one of said two pre-shaped hollow tubes to the proximal end of the second two pre-shaped hollow tubes opening.

It is another object of the present invention to provide the transcarotid access device as defined above, wherein said at least one continuous passage configured to automatically guide said suture from the proximal end of at least one of said two pre-shaped hollow tubes to the proximal end of the second two pre-shaped hollow tubes opening, when said suture is inserted and advanced through said at least one continuous passage.

It is another object of the present invention to provide the transcarotid access device as defined above, wherein the distal ends of said two pre-shaped hollow tubes, upon deployment out of said closure device and into said blood vessel are substantially aligned, such that a suture being threaded through at least one of said pre-shaped hollow tube can be extracted from the second pre-shaped hollow tube.

It is another object of the present invention to provide the transcarotid access device as defined above, wherein said at least two pre-shaped hollow tubes are positioned externally to said main sheath.

It is another object of the present invention to provide the transcarotid access device as defined above, wherein said at least two pre-shaped hollow tubes are positioned internally within said main sheath.

T It is another object of the present invention to provide the transcarotid access device as defined above, wherein at least one of said pre-shaped channels is characterized by a cross sectional area being at least one selected from a group consisting of circular, oval, rectangular, triangular and any combination thereof.

It is another object of the present invention to provide the transcarotid access device as defined above, wherein each of said distal ends of said pre-shaped hollow tubes additionally comprising magnetic means.

It is another object of the present invention to provide the transcarotid access device as defined above, wherein said magnetic means facilitates said engagement between said distal ends of said two pre-shaped hollow tubes by means of magnetic attraction.

It is another object of the present invention to provide the transcarotid access device as defined above, wherein at least one of said distal ends of said pre-shaped hollow tubes is cone-shaped.

It is another object of the present invention to provide the transcarotid access device as defined above, wherein said cone-shape facilitates said engagement between said distal ends of said two pre-shaped hollow tubes and ensure alignment therebetween.

It is another object of the present invention to provide the transcarotid access device as defined above, wherein at least one of said pre-shaped hollow tubes is characterized by a smaller cross-sectional area than the second pre-shaped hollow tube.

It is another object of the present invention to provide the transcarotid access device as defined above, wherein the distal end of said smaller cross-sectional area tube is introduced into the second pre-shaped hollow tube.

It is another object of the present invention to provide the transcarotid access device as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is another object of the present invention to provide the transcarotid access device as defined above, wherein said suture comprises ratchet mechanism, adapted to be secured on the carotid artery and suture the same.

It is another object of the present invention to provide the transcarotid access device as defined above, wherein said suture comprises at least one anchor, adapted to be secured on the carotid artery wall and suture the same.

It is another object of the present invention to provide the transcarotid access device as defined above, additionally comprising at least one alignment element adapted to facilitate alignment between said two pre-shaped hollow tubes.

It is another object of the present invention to provide the transcarotid access device as defined above, wherein said at least one alignment element comprises at least one arc-shaped groove, adapted to at least partially accommodate the distal end of both said two pre-shaped hollow tubes so as to facilitate alignment between said two pre-shaped hollow tubes.

It is another object of the present invention to provide the transcarotid access device as defined above, additionally comprising a guide wire.

It is another object of the present invention to provide the transcarotid access device as defined above, additionally comprising a foot fixation element adapted to engage with said guide wire and to fixate the orientation thereof such that no interference between said guide wire and said two pre-shaped hollow tubes is provided and to secure the walls of said vessel to said distal end of said transcarotid access device.

It is another object of the present invention to provide the transcarotid access device as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration and to engage only with the internal surface of said at least one blood vessel.

It is another object of the present invention to provide the transcarotid access device as defined above, wherein said at least one foot fixation element is characterized by a blunt edge to prevent any unwanted damage to said at least one blood vessel upon introduction therewithin.

It is another object of the present invention to provide the transcarotid access device as defined above, wherein said at least one foot fixation element is adapted to provide counter force to entry of said at least two pre-shaped hollow tubes.

It is another object of the present invention to provide the transcarotid access device as defined above, wherein deployment of said pre-shaped hollow tubes is either automatically, manually or semi-automatically/semi-manually provided by at least one handle provided at the proximal end of the device.

It is another object of the present invention to provide the transcarotid access device as defined above, wherein said at least one of said at least two pre-shaped hollow tubes are characterized by a rough surface.

It is another object of the present invention to provide the transcarotid access device as defined above, wherein the procedure is performed under at least one selected from ultrasound vision, fluoroscopy and any combination thereof.

It is another object of the present invention to provide the transcarotid access device as defined above, additionally comprising at least one sensor adapted to at least one selected from a group selected from (a) engagement of said at least two pre-shaped hollow tubes; (b) disengagement of said at least two pre-shaped hollow tubes; (c) any combination thereof.

It is another object of the present invention to provide a method for accessing and treating a carotid artery, comprising steps of:

a. obtaining a transcarotid access device according any of the above; said transcarotid access device comprising: a closure device having a proximal end and a distal end, introduced into a blood vessel, said distal end and said proximal end are interconnected by main sheath, said closure device comprising at least two pre-shaped hollow tubes, each of which having a proximal end, substantially at said proximal end of said closure device and a distal end; wherein said method additionally comprising steps of:
b. at least partially introducing said distal end of said device into said carotid artery;
c. at least partially introducing said two pre-shaped hollow tubes from said distal end of said closure device into said artery thereby at least partially deploying the distal ends of said two pre-shaped hollow tubes out of said main sheath and within said artery;
d. fully deploying said two pre-shaped hollow tubes out of said closure device, within said artery thereby (i) engaging into mechanical contact said distal ends of said two pre-shaped hollow tubes; and, (ii) substantially aligning said distal ends of said two pre-shaped hollow tubes;
e. when needed, suturing said artery by at least once threading a suture being through at least one of said pre-shaped hollow tube and extracted the same from the second pre-shaped hollow tube.

It is another object of the present invention to provide the method as defined above, additionally comprising step of percutaneously forming a transcervical access site in a neck of a patient to form an entryway through a wall of a common carotid artery.

It is another object of the present invention to provide the method as defined above, additionally comprising step of aspirating blood from the internal carotid artery by means of at least one reverse flow means.

It is another object of the present invention to provide the method as defined above, wherein said step of aspirating blood additionally comprising step of actively pumping blood from said carotid artery.

It is another object of the present invention to provide the method as defined above, additionally comprising step of inflating at least one balloon adapted to occlude the blood vessel.

It is another object of the present invention to provide the method as defined above, additionally comprising step of performing a surgical procedure within the blood vessel.

It is another object of the present invention to provide the method as defined above, wherein said surgical procedure is at least one selected from a group consisting of angioplasty, stenting, clot retrieval for stroke or heart attack, embolic protection, stroke prevention, brain aneurysm embolization, uterine embolization, angiodysplasia embolization in the bowel for bleeding, varicocele embolization, tumor embolization, visceral aneurysm embolization and any combination thereof.

It is another object of the present invention to provide the method as defined above, wherein said surgical procedure is performed while generating suction through said transcarotid access device.

It is another object of the present invention to provide the method as defined above, wherein said step of actively pumping blood from said carotid artery is performed to a return site.

It is another object of the present invention to provide the method as defined above, wherein the return site is a venous return site.

It is another object of the present invention to provide the method as defined above, wherein the return site is an external reservoir.

It is another object of the present invention to provide the method as defined above, wherein the reverse flow means is a syringe.

It is another object of the present invention to provide the method as defined above, wherein the external reservoir is a syringe.

It is another object of the present invention to provide the method as defined above, additionally comprising step of placing a distal embolic filter and positioning the same distaly to a treatment site in said carotid artery.

It is another object of the present invention to provide the method as defined above, additionally comprising step of placing at least one filter for filtering blood being introduced back into the patient's body.

It is another object of the present invention to provide the method as defined above, additionally comprising step of inserting a stent into a treatment site in said carotid artery.

It is another object of the present invention to provide the method as defined above, wherein the distal end of each of said pre-shaped hollow tubes is characterized by at least two configurations:

a. a first configuration, in which said pre-shaped hollow tube is at least partially housed within said main sheath; and,
b. a second configuration, in which said pre-shaped hollow tube is extended and protruding out of the distal end of said closure device, and characterized by having a curved shape.

It is another object of the present invention to provide the method as defined above, wherein each of said pre-shaped hollow tubes is convertible from said first configuration to said second configuration by linearly reciprocally moving each of said pre-shaped hollow tubes within said main sheath either towards said proximal end or distal end of said closure device.

It is another object of the present invention to provide the method as defined above, wherein said mechanical engagement of said two pre-shaped hollow tubes results in at least one continuous passage between the proximal end of at least one of said two pre-shaped hollow tubes to the proximal end of the second two pre-shaped hollow tubes opening.

It is another object of the present invention to provide the method as defined above, wherein said at least one continuous passage configured to automatically guide said suture from the proximal end of at least one of said two pre-shaped hollow tubes to the proximal end of the second two pre-shaped hollow tubes opening, when said suture is inserted and advanced through said at least one continuous passage.

It is another object of the present invention to provide the method as defined above, wherein the distal ends of said two pre-shaped hollow tubes, upon deployment out of said closure device and into said blood vessel are substantially aligned, such that a suture being threaded through at least one of said pre-shaped hollow tube can be extracted from the second pre-shaped hollow tube.

It is another object of the present invention to provide the method as defined above, wherein at least one of said pre-shaped channels is characterized by a cross sectional area being at least one selected from a group consisting of circular, oval, rectangular, triangular and any combination thereof.

It is another object of the present invention to provide the method as defined above, wherein each of said distal ends of said pre-shaped hollow tubes additionally comprising magnetic means.

It is another object of the present invention to provide the method as defined above, wherein said magnetic means facilitates said engagement between said distal ends of said two pre-shaped hollow tubes by means of magnetic attraction.

In some embodiments of the method, at least one of said distal ends of said pre-shaped hollow tubes is cone-shaped.

It is another object of the present invention to provide the method as defined above, wherein said cone-shape facilitates said engagement between said distal ends of said two pre-shaped hollow tubes and ensure alignment therebetween.

It is another object of the present invention to provide the method as defined above, wherein at least one of said pre-shaped hollow tubes is characterized by a smaller cross-sectional area than the second pre-shaped hollow tube.

It is another object of the present invention to provide the method as defined above, wherein the distal end of said smaller cross-sectional area tube is introduced into the second pre-shaped hollow tube.

It is another object of the present invention to provide the method as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is another object of the present invention to provide the method as defined above, wherein said suture comprises ratchet mechanism, adapted to be secured on said artery and suture the same.

It is another object of the present invention to provide the method as defined above, wherein said suture comprises at least one anchor, adapted to be secured on said artery wall and suture the same.

It is another object of the present invention to provide the method as defined above, additionally comprising at least one alignment element adapted to facilitate alignment between said two pre-shaped hollow tubes.

It is another object of the present invention to provide the method as defined above, wherein said at least one alignment element comprises at least one arc-shaped groove, adapted to at least partially accommodate the distal end of both said two pre-shaped hollow tubes so as to facilitate alignment between said two pre-shaped hollow tubes.

It is another object of the present invention to provide the method as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration and to engage only with the internal surface of said at least one blood vessel.

It is another object of the present invention to provide the method as defined above, wherein said at least one foot fixation element is characterized by a blunt edge to prevent any unwanted damage to said at least one blood vessel upon introduction therewithin.

It is another object of the present invention to provide the method as defined above, wherein said at least one foot fixation element is adapted to provide counter force to entry of said at least two pre-shaped hollow tubes.

It is another object of the present invention to provide the method as defined above, wherein deployment of said pre-shaped hollow tubes is either automatically, manually or semi-automatically/semi-manually provided by at least one handle provided at the proximal end of the device.

It is another object of the present invention to provide the method as defined above, additionally comprising step of disengaging the coupling said two pre-shaped hollow tubes and retracting at least one of which outside said at least one blood vessel.

It is another object of the present invention to provide the method as defined above, wherein said at least one of said at least two pre-shaped hollow tubes are characterized by a rough surface.

It is another object of the present invention to provide the method as defined above, wherein the procedure is performed under at least one selected from ultrasound vision, fluoroscopy and any combination thereof.

It is another object of the present invention to provide the method as defined above, additionally comprising at least one sensor adapted to at least one selected from a group selected from (a) engagement of said at least two pre-shaped hollow tubes; (b) disengagement of said at least two pre-shaped hollow tubes; (c) any combination thereof.

It is another object of the present invention to provide a closure device having a proximal end and a distal end, introduced into a blood vessel, comprising a pre-shaped hollow tube having a proximal end, substantially at said proximal end of said closure device and a distal end, adapted to be introduced from said distal end of said closure device into said blood vessel at a predetermined first location;

wherein, said pre-shape form is a U-shape;

further wherein upon deployment of said pre-shaped hollow tube out of said closure device, within said blood vessel, said distal end thereof is adapted to assume said pre-shape form and exit said blood vessel, at predetermined second location, back into said closure device and the proximal end thereof, and to enable a suture, being threaded through said pre-shaped hollow tube at said at predetermined first location, to be extracted from the blood vessel at said at predetermined second location.

It is another object of the present invention to provide the closure device as defined above, wherein suture is in communication with a flexible needle.

It is another object of the present invention to provide the closure device as defined above, wherein said distal ends of said pre-shaped hollow tube is sharp so as to enable introduction into and extraction out of said blood vessel.

It is another object of the present invention to provide the closure device as defined above, wherein said suture comprises ratchet mechanism, adapted to be secured on said blood vessel and suture the same.

It is another object of the present invention to provide the closure device as defined above, wherein said suture comprises at least one anchor, adapted to be secured on said blood vessel wall and suture the same.

It is another object of the present invention to provide the closure device as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration.

It is another object of the present invention to provide the closure device as defined above, wherein said at least one foot fixation element is characterized by a blunt edge to prevent any unwanted damage to said at least one blood vessel upon introduction therewithin.

It is another object of the present invention to provide the closure device as defined above, wherein said at least one foot fixation element is adapted to provide counter force to entry of said pre-shaped hollow tube.

It is another object of the present invention to provide the closure device as defined above, wherein said pre-shaped hollow tube is characterized by a rough surface.

It is another object of the present invention to provide the closure device as defined above, wherein the procedure is performed under at least one selected from ultrasound vision, fluoroscopy and any combination thereof.

It is another object of the present invention to provide a method of suturing at least one blood vessel, comprising steps of:

a. obtaining a closure device having a proximal end and a distal end, introduced into a blood vessel, comprising a pre-shaped hollow tube having a proximal end, substantially at said proximal end of said closure device and a distal end, adapted to be introduced from said distal end of said closure device into said blood vessel at a predetermined first location; wherein, said pre-shape form is a U-shape;
b. introducing said distal end of said device into said blood vessel;
c. at least partially introducing said pre-shaped hollow tube from said distal end of said closure device into said blood vessel; thereby said pre-shaped hollow tube assumes its pre-shape form;
d. further introducing said pre-shaped hollow tube; thereby extracting said distal end of said pre-shaped hollow tube from said blood vessel at predetermined second location;
e. suturing said blood vessel by at least once threading a suture being through said pre-shaped hollow tube into said blood vessel at said predetermined first location and extracted the same from said predetermined second location.

It is another object of the present invention to provide the method as defined above, wherein suture is in communication with a flexible needle.

It is another object of the present invention to provide the method as defined above, wherein said distal ends of said pre-shaped hollow tube is sharp so as to enable introduction into and extraction out of said blood vessel.

It is another object of the present invention to provide the method as defined above, wherein said suture comprises ratchet mechanism, adapted to be secured on said blood vessel and suture the same.

It is another object of the present invention to provide the method as defined above, wherein said suture comprises at least one anchor, adapted to be secured on said blood vessel wall and suture the same.

It is another object of the present invention to provide the method as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration.

It is another object of the present invention to provide the method as defined above, wherein said at least one foot fixation element is characterized by a blunt edge to prevent any unwanted damage to said at least one blood vessel upon introduction therewithin.

It is another object of the present invention to provide the method as defined above, wherein said at least one foot fixation element is adapted to provide counter force to entry of said at least two pre-shaped hollow tubes.

It is another object of the present invention to provide the method as defined above, wherein deployment of said pre-shaped hollow tube is either automatically, manually or semi-automatically/semi-manually provided by at least one handle provided at the proximal end of the device.

It is another object of the present invention to provide the method as defined above, additionally comprising step of retracting said pre-shaped hollow tube outside said at least one blood vessel.

It is another object of the present invention to provide the method as defined above, wherein said pre-shaped hollow tube is characterized by a rough surface.

It is another object of the present invention to provide the method as defined above, wherein the procedure is performed under at least one selected from ultrasound vision, fluoroscopy and any combination thereof.

It is another object of the present invention to provide a transcarotid access device, comprising the closure device as any of the described above.

It is another object of the present invention to provide the transcarotid access device as defined above, wherein said suture comprises ratchet mechanism, adapted to be secured on the carotid artery and suture the same.

It is another object of the present invention to provide the transcarotid access device as defined above, wherein said suture comprises at least one anchor, adapted to be secured on the carotid artery wall and suture the same.

It is another object of the present invention to provide the transcarotid access device as defined above, additionally comprising a guide wire.

It is another object of the present invention to provide the transcarotid access device as defined above, additionally comprising a foot fixation element adapted to engage with said guide wire and to fixate the orientation thereof such that no interference between said guide wire and said two pre-shaped hollow tubes is provided.

It is another object of the present invention to provide the transcarotid access device as defined above, additionally comprising a foot fixation element adapted to secure the walls of said vessel to said distal end of said transcarotid access device.

It is another object of the present invention to provide the transcarotid access device as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration.

It is another object of the present invention to provide the transcarotid access device as defined above, wherein said at least one foot fixation element is characterized by a blunt edge to prevent any unwanted damage to said at least one blood vessel upon introduction therewithin.

It is another object of the present invention to provide the transcarotid access device as defined above, wherein said at least one foot fixation element is adapted to provide counter force to entry of said pre-shaped hollow tube.

It is another object of the present invention to provide the transcarotid access device as defined above, wherein deployment of said pre-shaped hollow tube is either automatically, manually or semi-automatically/semi-manually provided by at least one handle provided at the proximal end of the device.

It is another object of the present invention to provide the transcarotid access device as defined above, wherein said pre-shaped hollow tube is characterized by a rough surface.

It is another object of the present invention to provide the transcarotid access device as defined above, wherein the procedure is performed under at least one selected from ultrasound vision, fluoroscopy and any combination thereof.

It is another object of the present invention to provide a method for accessing and treating a carotid artery, comprising steps of:

a. obtaining a closure device having a proximal end and a distal end, introduced into an artery, comprising a pre-shaped hollow tube having a proximal end, substantially at said proximal end of said closure device and a distal end, adapted to be introduced from said distal end of said closure device into said artery at a predetermined first location; and, a guide wire; wherein, said pre-shape form is a U-shape;
b. introducing a guide wire into said carotid artery;
c. introducing said distal end of said device into said carotid artery;
d. at least partially introducing said pre-shaped hollow tube from said distal end of said closure device into said artery; thereby said pre-shaped hollow tube assumes its pre-shape form;
e. further introducing said pre-shaped hollow tube; thereby extracting said distal end of said pre-shaped hollow tube from said artery at predetermined second location;
f. suturing said artery by at least once threading a suture being through said pre-shaped hollow tube into said artery at said predetermined first location and extracted the same from said predetermined second location.

It is another object of the present invention to provide the method as defined above, additionally comprising step of percutaneously forming a transcervical access site in a neck of a patient to form an entryway through a wall of a common carotid artery.

It is another object of the present invention to provide the method as defined above, additionally comprising step of aspirating blood from the internal carotid artery.

It is another object of the present invention to provide the method as defined above, wherein said step of aspirating blood additionally comprising step of actively pumping blood from said carotid artery.

It is another object of the present invention to provide the method as defined above, wherein said step of step of actively pumping blood from said carotid artery is performed to a return site.

It is another object of the present invention to provide the method as defined above, wherein the return site is a venous return site.

It is another object of the present invention to provide the method as defined above, wherein the return site is an external reservoir.

It is another object of the present invention to provide the method as defined above, wherein the return site is a device that performs the aspiration.

It is another object of the present invention to provide the method as defined above, wherein the aspiration device is a syringe.

It is another object of the present invention to provide the method as defined above, wherein the external reservoir is a syringe.

It is another object of the present invention to provide the method as defined above, additionally comprising step of placing a distal embolic filter and positioning the same distaly to a treatment site in said carotid artery.

It is another object of the present invention to provide the method as defined above, additionally comprising step of placing at least one filter for filtering blood being introduced back into the patient's body.

It is another object of the present invention to provide the method as defined above, additionally comprising step of performing a treatment at the treatment site.

It is another object of the present invention to provide the method as defined above, additionally comprising step of inserting a stent into a treatment site in said carotid artery.

It is another object of the present invention to provide the method as defined above, additionally comprising step of extracting said guide wire.

It is another object of the present invention to provide the method as defined above, wherein said suture comprises ratchet mechanism, adapted to be secured on said artery and suture the same.

It is another object of the present invention to provide the method as defined above, wherein said suture comprises at least one anchor, adapted to be secured on said artery wall and suture the same.

It is another object of the present invention to provide the method as defined above, additionally comprising at least one foot fixation element characterized by at least two configurations, a retracted configuration in which the same is substantially perpendicular to said at least one blood vessel and a deployed configuration in which the same is substantially parallel to said at least one blood vessel, adapted upon introduction to said at least one blood vessel to retain said deployed configuration.

It is another object of the present invention to provide the method as defined above, wherein said at least one foot fixation element is characterized by a blunt edge to prevent any unwanted damage to said at least one blood vessel upon introduction therewithin.

It is another object of the present invention to provide the method as defined above, wherein said at least one foot fixation element is adapted to provide counter force to entry of said pre-shaped hollow tube.

It is another object of the present invention to provide the method as defined above, wherein deployment of said pre-shaped hollow tubes is either automatically, manually or semi-automatically/semi-manually provided by at least one handle provided at the proximal end of the device.

It is another object of the present invention to provide the method as defined above, additionally comprising step of disengaging the retracting said pre-shaped hollow tube outside said at least one blood vessel.

It is another object of the present invention to provide the method as defined above, wherein said pre-shaped hollow tube is characterized by a rough surface.

It is another object of the present invention to provide the method as defined above, wherein the procedure is performed under at least one selected from ultrasound vision, fluoroscopy and any combination thereof.

It is therefore one object of the present invention to disclose a closure device having a proximal end and a distal end, introduced into a blood vessel, comprising at least two pre-shaped hollow tubes having a proximal end, substantially at said proximal end of said closure device and a distal end, adapted to be introduced from said distal end of said closure device into said blood vessel; wherein, upon deployment of said two pre-shaped hollow tubes out of said closure device, within said blood vessel, said distal ends thereof are adapted to (i) engage into mechanical contact; and, (ii) substantially align therebetween, such that a suture being threaded through at least one of said pre-shaped hollow tube can be extracted from the second pre-shaped hollow tube.

It is another object of the present invention to disclose the closure device as defined above, wherein at least one of said pre-shaped channels is characterized by a cross sectional area being at least one selected from a group consisting of circular, oval, rectangular, triangular and any combination thereof.

It is another object of the present invention to disclose the closure device as defined above, wherein each of said distal ends of said pre-shaped hollow tubes additionally comprising magnetic means.

It is another object of the present invention to disclose the closure device as defined above, wherein said magnetic means facilitates said engagement between said distal ends of said two pre-shaped hollow tubes by means of magnetic attraction.

It is another object of the present invention to disclose the closure device as defined above, wherein at least one of said distal ends of said pre-shaped hollow tubes is cone-shaped.

It is another object of the present invention to disclose the closure device as defined above, wherein said cone-shape facilitates said engagement between said distal ends of said two pre-shaped hollow tubes and ensure alignment therebetween.

It is another object of the present invention to disclose the closure device as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is another object of the present invention to disclose the closure device as defined above, wherein said suture comprises mechanism, adapted to be secured on said blood vessel and suture the same.

It is another object of the present invention to disclose the closure device as defined above, wherein said suture comprises at least one anchor, adapted to be secured on said blood vessel wall and suture the same.

It is another object of the present invention to disclose a method of suturing at least one blood vessel, comprising steps of:

a. obtaining a closure device having a proximal end and a distal end, introduced into a blood vessel, comprising at least two pre-shaped hollow tubes having a proximal end, substantially at said proximal end of said closure device and a distal end;
b. introducing said distal end of said device into said blood vessel;
c. at least partially introducing said two pre-shaped hollow tubes from said distal end of said closure device into said blood vessel thereby at least partially deploying said two pre-shaped hollow tubes within said blood vessel;
d. fully deploying said two pre-shaped hollow tubes out of said closure device, within said blood vessel thereby (i) engaging into mechanical contact said distal ends of said two pre-shaped hollow tubes; and, (ii) substantially aligning said distal ends of said two pre-shaped hollow tubes;
e. suturing said blood vessel by at least once threading a suture being through at least one of said pre-shaped hollow tube and extracted the same from the second pre-shaped hollow tube.

It is another object of the present invention to disclose the method as defined above, wherein at least one of said pre-shaped channels is characterized by a cross sectional area being at least one selected from a group consisting of circular, oval, rectangular, triangular and any combination thereof.

It is another object of the present invention to disclose the method as defined above, wherein each of said distal ends of said pre-shaped hollow tubes additionally comprising magnetic means.

It is another object of the present invention to disclose the method as defined above, wherein said magnetic means facilitates said engagement between said distal ends of said two pre-shaped hollow tubes by means of magnetic attraction.

It is another object of the present invention to disclose the method as defined above, wherein at least one of said distal ends of said pre-shaped hollow tubes is cone-shaped.

It is another object of the present invention to disclose the method as defined above, wherein said cone-shape facilitates said engagement between said distal ends of said two pre-shaped hollow tubes and ensure alignment therebetween.

It is another object of the present invention to disclose the method as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is another object of the present invention to disclose the method as defined above, wherein said suture comprises ratchet mechanism, adapted to be secured on said blood vessel and suture the same.

It is another object of the present invention to disclose the method as defined above, wherein said suture comprises at least one anchor, adapted to be secured on said blood vessel wall and suture the same.

It is another object of the present invention to disclose at least one selected from a group consisting of transcarotid access device, femoral carotid access device, jugular carotid access device, comprising the closure device as defined above.

It is another object of the present invention to disclose the device as defined above, wherein at least one of said pre-shaped channels is characterized by a cross sectional area being at least one selected from a group consisting of circular, oval, rectangular, triangular and any combination thereof.

It is another object of the present invention to disclose the device as defined above, wherein each of said distal ends of said pre-shaped hollow tubes additionally comprising magnetic means.

It is another object of the present invention to disclose the device as defined above, wherein said magnetic means facilitates said engagement between said distal ends of said two pre-shaped hollow tubes by means of magnetic attraction.

It is another object of the present invention to disclose the device as defined above, wherein at least one of said distal ends of said pre-shaped hollow tubes is cone-shaped.

It is another object of the present invention to disclose the device as defined above, wherein said cone-shape facilitates said engagement between said distal ends of said two pre-shaped hollow tubes and ensure alignment therebetween.

It is another object of the present invention to disclose the device as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is another object of the present invention to disclose the device as defined above, wherein said suture comprises ratchet mechanism, adapted to be secured on the carotid artery and suture the same.

It is another object of the present invention to disclose the device as defined above, wherein said suture comprises at least one anchor, adapted to be secured on the carotid artery wall and suture the same.

It is another object of the present invention to disclose the device as defined above, additionally comprising a guide wire.

It is another object of the present invention to disclose the device as defined above, additionally comprising a foot fixation element adapted to engage with said guide wire and to fixate the orientation thereof such that no interference between said guide wire and said two pre-shaped hollow tubes is provided.

It is another object of the present invention to disclose the device as defined above, additionally comprising a foot fixation element adapted to secure the walls of said vessel to said distal end of said device.

It is another object of the present invention to disclose a method for accessing and treating a carotid artery, comprising a. obtaining a closure device having a proximal end and a distal end, introduced into an artery, comprising at least two pre-shaped hollow tubes having a proximal end, substantially at said proximal end of said closure device and a distal end; and, a guide wire;
b. introducing a guide wire into said carotid artery;
c. introducing said distal end of said device into said carotid artery;
d.
e. at least partially introducing said two pre-shaped hollow tubes from said distal end of said closure device into said artery thereby at least partially deploying said two pre-shaped hollow tubes within said artery;

f. fully deploying said two pre-shaped hollow tubes out of said closure device, within said artery thereby (i) engaging into mechanical contact said distal ends of said two pre-shaped hollow tubes; and, (ii) substantially aligning said distal ends of said two pre-shaped hollow tubes;

g. when needed, suturing said artery by at least once threading a suture being through at least one of said pre-shaped hollow tube and extracted the same from the second pre-shaped hollow tube.

It is another object of the present invention to disclose the method as defined above, additionally comprising step of percutaneously forming a transcervical access site in a neck of a patient to form an entryway through a wall of a common carotid artery.

It is another object of the present invention to disclose the method as defined above, additionally comprising step of aspirating blood from the internal carotid artery.

It is another object of the present invention to disclose the method as defined above, wherein said step of aspirating blood additionally comprising step of actively pumping blood from said carotid artery.

It is another object of the present invention to disclose the method as defined above, wherein said step of step of actively pumping blood from said carotid artery is performed to a return site.

It is another object of the present invention to disclose the method as defined above, wherein the return site is a venous return site.

It is another object of the present invention to disclose the method as defined above, wherein the return site is an external reservoir.

It is another object of the present invention to disclose the method as defined above, wherein the return site is a device that performs the aspiration.

It is another object of the present invention to disclose the method as defined above, wherein the aspiration device is a syringe.

It is another object of the present invention to disclose the method as defined above, wherein the external reservoir is a syringe.

It is another object of the present invention to disclose the method as defined above, additionally comprising step of placing a distal embolic filter and positioning the same distaly to a treatment site in said carotid artery.

It is another object of the present invention to disclose the method as defined above, additionally comprising step of placing at least one filter for filtering blood being introduced back into the patient's body.

It is another object of the present invention to disclose the method as defined above, additionally comprising step of performing a treatment at the treatment site.

It is another object of the present invention to disclose the method as defined above, additionally comprising step of inserting a stent into a treatment site in said carotid artery.

It is another object of the present invention to disclose the method as defined above, additionally comprising step of extracting said guide wire.

It is another object of the present invention to disclose the method as defined above, wherein at least one of said pre-shaped channels is characterized by a cross sectional area being at least one selected from a group consisting of circular, oval, rectangular, triangular and any combination thereof.

It is another object of the present invention to disclose the method as defined above, wherein each of said distal ends of said pre-shaped hollow tubes additionally comprising magnetic means.

It is another object of the present invention to disclose the method as defined above, wherein said magnetic means facilitates said engagement between said distal ends of said two pre-shaped hollow tubes by means of magnetic attraction.

It is another object of the present invention to disclose the method as defined above, wherein at least one of said distal ends of said pre-shaped hollow tubes is cone-shaped.

It is another object of the present invention to disclose the method as defined above, wherein said cone-shape facilitates said engagement between said distal ends of said two pre-shaped hollow tubes and ensure alignment therebetween.

It is another object of the present invention to disclose the method as defined above, wherein at least one of said distal ends of said pre-shaped hollow tubes additionally comprising at least one mechanical mechanism, adapted to secure the engagement between said distal ends of said two pre-shaped hollow tubes and ensure alignment therebetween.

It is still an object of the present invention to disclose the method as defined above, wherein said suture comprises ratchet mechanism, adapted to be secured on said artery and suture the same.

It is lastly object of the present invention to disclose the method as defined above, wherein said suture comprises at least one anchor, adapted to be secured on said artery wall and suture the same.

It is another object of the present invention to provide a closure device having a proximal end and a distal end, introduced into a blood vessel, comprising a pre-shaped hollow tube having a proximal end, substantially at said proximal end of said closure device and a distal end, adapted to be introduced from said distal end of said closure device into said blood vessel at a predetermined first location;

wherein, said pre-shape form is a U-shape;

further wherein upon deployment of said pre-shaped hollow tube out of said closure device, within said blood vessel, said distal end thereof is adapted to assume said pre-shape form and exit said blood vessel, at predetermined second location, back into said closure device and the proximal end thereof, and to enable a suture, being threaded through said pre-shaped hollow tube at said at predetermined first location, to be extracted from the blood vessel at said at predetermined second location.

It is another object of the present invention to provide the closure device as defined above, wherein suture is in communication with a flexible needle.

It is another object of the present invention to provide the closure device as defined above, wherein said distal ends of said pre-shaped hollow tube is sharp so as to enable introduction into and extraction out of said blood vessel.

It is another object of the present invention to provide the closure device as defined above, wherein said suture comprises ratchet mechanism, adapted to be secured on said blood vessel and suture the same.

It is another object of the present invention to provide the closure device as defined above, wherein said suture comprises at least one anchor, adapted to be secured on said blood vessel wall and suture the same.

It is another object of the present invention to provide a method of suturing at least one blood vessel, comprising steps of:

a. obtaining a closure device having a proximal end and a distal end, introduced into a blood vessel, comprising a pre-shaped hollow tube having a proximal end, substantially at said proximal end of said closure device and a distal end, adapted to be introduced from said distal end of said closure device into said blood vessel at a predetermined first location; wherein, said pre-shape form is a U-shape;

b. introducing said distal end of said device into said blood vessel;

c. at least partially introducing said pre-shaped hollow tube from said distal end of said closure device into said blood vessel; thereby said pre-shaped hollow tube assumes its pre-shape form;

d. further introducing said pre-shaped hollow tube; thereby extracting said distal end of said pre-shaped hollow tube from said blood vessel at predetermined second location;

e. suturing said blood vessel by at least once threading a suture being through said pre-shaped hollow tube into said blood vessel at said predetermined first location and extracted the same from said predetermined second location.

It is another object of the present invention to provide the method as defined above, wherein suture is in communication with a flexible needle.

It is another object of the present invention to provide the method as defined above, wherein said distal ends of said pre-shaped hollow tube is sharp so as to enable introduction into and extraction out of said blood vessel.

It is another object of the present invention to provide the method as defined above, wherein said suture comprises ratchet mechanism, adapted to be secured on said blood vessel and suture the same.

It is another object of the present invention to provide the method as defined above, wherein said suture comprises at least one anchor, adapted to be secured on said blood vessel wall and suture the same.

It is another object of the present invention to provide at least one selected from a group consisting of transcarotid access device, femoral carotid access device, jugular carotid access device, comprising the closure device as defined above.

It is another object of the present invention to provide the device as defined above, wherein said suture comprises ratchet mechanism, adapted to be secured on the carotid artery and suture the same.

It is another object of the present invention to provide the device as defined above, wherein said suture comprises at least one anchor, adapted to be secured on the carotid artery wall and suture the same.

It is another object of the present invention to provide the device as defined above, additionally comprising a guide wire.

It is another object of the present invention to provide the device as defined above, additionally comprising a foot fixation element adapted to engage with said guide wire and to fixate the orientation thereof such that no interference between said guide wire and said two pre-shaped hollow tubes is provided.

It is another object of the present invention to provide the device as defined above, additionally comprising a foot fixation element adapted to secure the walls of said vessel to said distal end of said device.

It is another object of the present invention to provide a method for accessing and treating a carotid artery, comprising steps of:

a. obtaining a closure device having a proximal end and a distal end, introduced into an artery, comprising a pre-shaped hollow tube having a proximal end, substantially at said proximal end of said closure device and a distal end, adapted to be introduced from said distal end of said closure device into said artery at a predetermined first location; and, a guide wire; wherein, said pre-shape form is a U-shape;

b. introducing a guide wire into said carotid artery;

c. introducing said distal end of said device into said carotid artery;

d. at least partially introducing said pre-shaped hollow tube from said distal end of said closure device into said artery; thereby said pre-shaped hollow tube assumes its pre-shape form;

e. further introducing said pre-shaped hollow tube; thereby extracting said distal end of said pre-shaped hollow tube from said artery at predetermined second location;

f. suturing said artery by at least once threading a suture being through said pre-shaped hollow tube into said artery at said predetermined first location and extracted the same from said predetermined second location.

It is another object of the present invention to provide the method as defined above, additionally comprising step of percutaneously forming a transcervical access site in a neck of a patient to form an entryway through a wall of a common carotid artery.

It is another object of the present invention to provide the method as defined above, additionally comprising step of aspirating blood from the internal carotid artery.

It is another object of the present invention to provide the method as defined above, wherein said step of aspirating blood additionally comprising step of actively pumping blood from said carotid artery.

It is another object of the present invention to provide the method as defined above, wherein said step of step of actively pumping blood from said carotid artery is performed to a return site.

It is another object of the present invention to provide the method as defined above, wherein the return site is a venous return site.

It is another object of the present invention to provide the method as defined above, wherein the return site is an external reservoir.

It is another object of the present invention to provide the method as defined above, wherein the return site is a device that performs the aspiration.

It is another object of the present invention to provide the method as defined above, wherein the aspiration device is a syringe.

It is another object of the present invention to provide the method as defined above, wherein the external reservoir is a syringe.

It is another object of the present invention to provide the method as defined above, additionally comprising step of placing a distal embolic filter and positioning the same distaly to a treatment site in said carotid artery.

It is another object of the present invention to provide the method as defined above, additionally comprising step of placing at least one filter for filtering blood being introduced back into the patient's body.

It is another object of the present invention to provide the method as defined above, additionally comprising step of performing a treatment at the treatment site.

It is another object of the present invention to provide the method as defined above, additionally comprising step of inserting a stent into a treatment site in said carotid artery.

It is another object of the present invention to provide the method as defined above, additionally comprising step of extracting said guide wire.

It is another object of the present invention to provide the method as defined above, wherein said suture comprises ratchet mechanism, adapted to be secured on said artery and suture the same.

It is lastly an object of the present invention to provide the method as defined above, wherein said suture comprises at least one anchor, adapted to be secured on said artery wall and suture the same.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and figures makes apparent to those skilled in the art how embodiments of the invention may be practiced.

In the drawings:

FIGS. 1A-1J illustrating the closure device 100, according to one embodiment of the present invention;

FIGS. 4A-4D illustrate a second embodiment of the present invention.

FIGS. 6A-6B illustrate an embodiment of the vascular catheter 10000 according to the present invention.

DESCRIPTION OF SPECIFIC EMBODIMENTS OF THE INVENTION

Figure 1C:
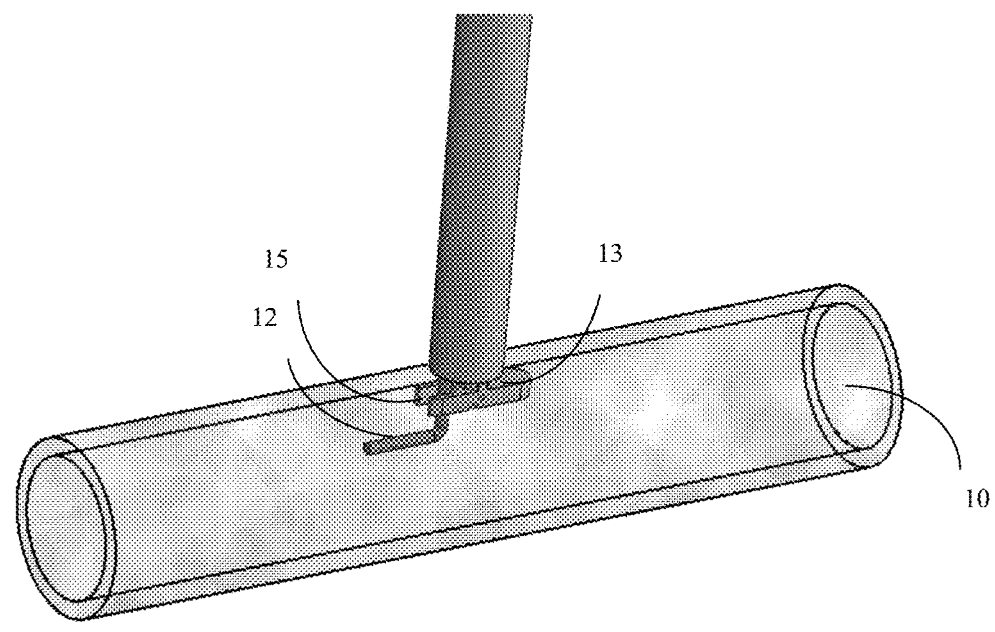
Figure 1D:
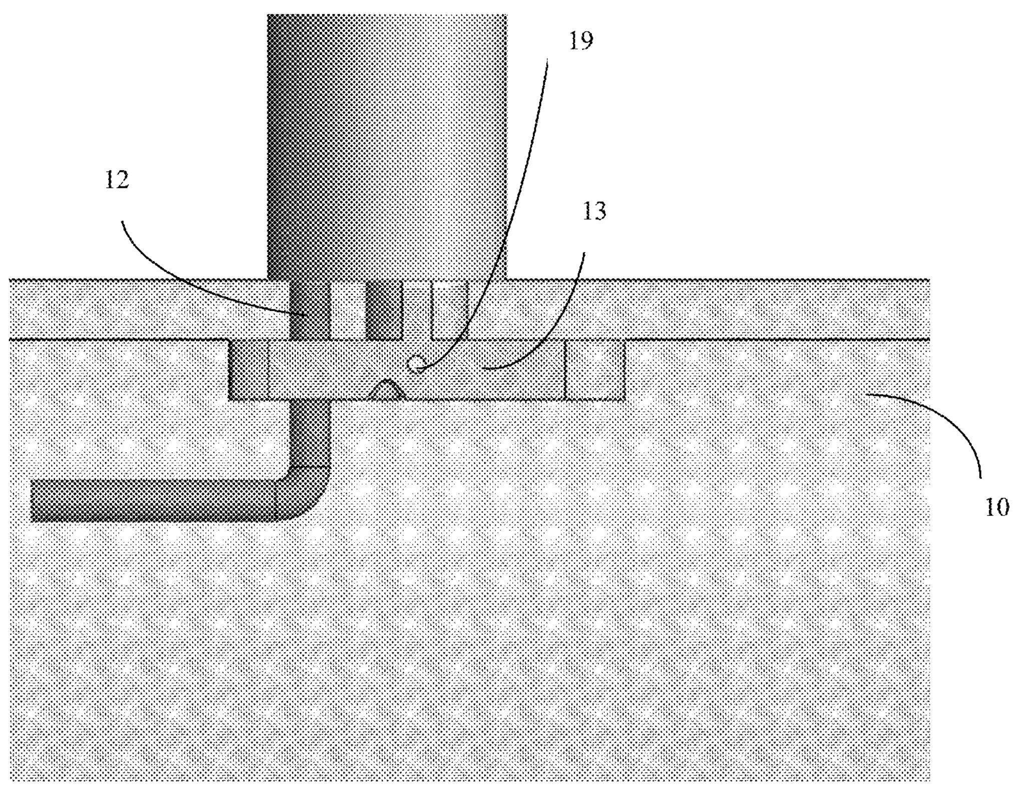
Figure 1D:
Figure 1E:
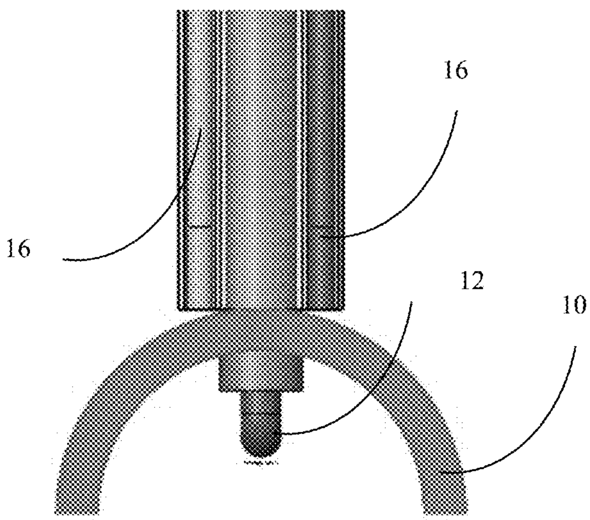
Figure 1F:
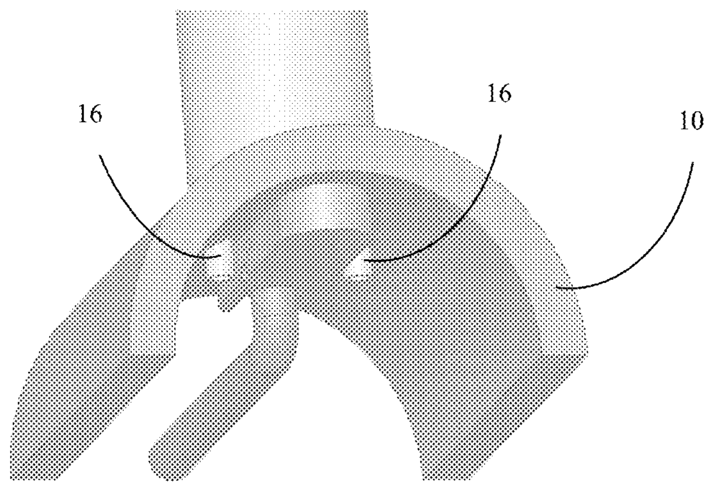
Figure 1G:
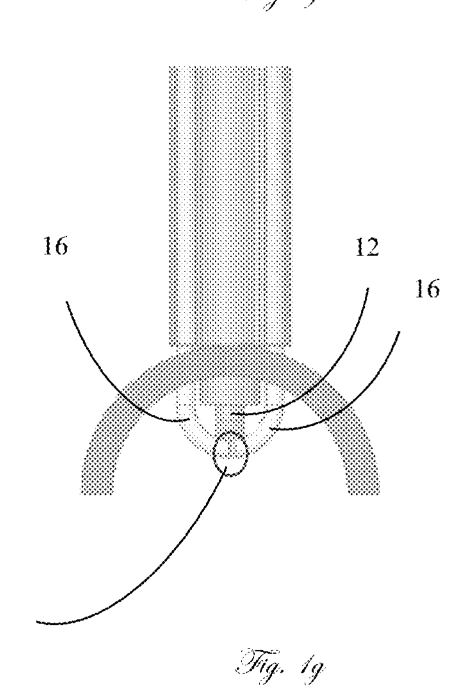

The present invention, in some embodiments thereof, relates to an interventional medical closure device, and to a method of performing an interventional procedure to effect closure of openings in blood vessels (namely arteries and veins).

In particular the invention relates to suturing/closure device specifically directed to the carotid arteries.

As used herein with reference to quantity or value, the term "about" means "within ±10% of".

As used herein the term "blood vessel" refers hereinafter to any of the five types of blood vessels: the arteries, which carry the blood away from the heart; the arterioles; the capillaries, where the exchange of water and chemicals between the blood and the tissues occurs; the venules; and the veins, which carry blood from the capillaries back towards the heart.

The terms "comprises", "comprising", "includes", "including", "has", "having" and their conjugates mean "including but not limited to".

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Overview

As disclosed above, the present further discloses a suturing device and method for closing blood vessels. More specifically, the present further discloses a device and method for closing an opening in the carotid arteries, post procedure; namely, carotid artery diseases.

The present invention further discloses interventional catheters such as for percutaneous trans carotid stenting to treat carotid artery disease.

Carotid Artery Diseases

Carotid artery disease usually consists of deposits of plaque which narrow the internal carotid artery ICA at or near the junction between the common carotid artery and the internal carotid artery. These deposits increase the risk of embolic particles being generated and entering the cerebral vasculature, leading to neurologic consequences such as transient ischemic attacks TIA, ischemic stroke, or death. In addition, should such narrowing become severe, blood flow to the brain is inhibited with serious and sometimes fatal consequences.

Two principal therapies are employed for treating carotid artery disease. The first is carotid endarterectomy CEA, an open surgical procedure which relies on clamping the common, internal and external carotid arteries, surgically opening the carotid artery at the site of the disease (usually the carotid bifurcation where the common carotid artery divides into the internal carotid artery and external carotid artery), dissecting away and removing the plaque, and then closing the carotid artery with a suture. The risk of emboli release into the internal and external arteries is minimized. During the procedure while the artery is opened, all the carotid artery branches are clamped so particles are unable to enter the vasculature. The arteries are debrided and vigorously flushed before closing the vessels and restoring blood flow. Because the clinical consequence of emboli release into the external carotid artery is less significant, the common carotid and external carotid arteries are usually unclamped first, so that any embolic particles which remain in the bifurcation or in the common carotid artery are flushed from the common carotid artery into the external carotid artery. As a last step, the internal carotid artery clamp is opened to restore arterial flow throughout the carotid circulation.

The second procedure, carotid artery stenting, CAS, relies on deployment and (self) expansion of a metallic stent across the carotid artery stenosis, typically at or across the branch from the common carotid artery into the internal carotid artery, or entirely in the internal carotid artery, depending on the position of the disease.

Usually, the self-expanding stent is introduced through a percutaneous puncture into the femoral artery in the groin and up the aortic arch into the target common carotid artery. If deemed necessary, a balloon dilatation of the stenosis is performed before the stent is inserted, to open the lesion and facilitate the placement of the stent delivery catheter and of other devices. In the majority of instances, a balloon dilatation is performed on the stenosis after the stent is placed, to optimize the luminal diameter of the stented segment. Usually, a guide wire remains in place across the stenosis during the entire intervention of the stenosis to facilitate the exchange of the various devices for pre-dilatation, stent delivery, and post-dilatation. The guide wire remains in place until a final angiogram confirms an acceptable outcome.

In carotid stenting procedures, there has been several methods proposed to at least partially alleviate the risk of emboli. One of the methods for reducing embolic risk during CAS procedures that have been proposed utilizes the concept of stopping or reversing the flow into the internal carotid artery to prevent embolic debris entering the cerebral vasculature. In a static flow method, the common carotid artery and external carotid artery are occluded during the intervention. An opening in the cannula between the occlusions is used to deliver the interventional devices into the target internal carotid artery. During periods of the intervention and at the end of the intervention prior to establishing forward flow in the internal carotid artery, aspiration is performed between the occlusions to remove embolic debris.

In reverse flow protocols, the arterial access cannula is connected to a venous cannula or to a low-pressure external receptacle in order to establish a reverse or retrograde flow from the internal carotid artery through the arterial cannula and away from the cerebral vasculature. After such reverse or retrograde flow is established, the stenting procedure may be performed with a greatly reduced risk of emboli entering the cerebral vasculature. Such an approach eliminates complications associated with gaining transfemoral endovascular access to the common carotid artery, and allows the possibility of much shorter and potentially larger profile interventional devices.

In addition, the shorter length reduces the flow resistance and thus increases the level of reverse flow achievable. This increased reverse flow can be helpful to remove the need to occlude the external carotid artery by reducing the potential flow from the external carotid artery antegrade to the internal carotid artery during common carotid artery occlusion in the case of an external carotid artery to internal carotid artery pressure gradient. The elimination of the external carotid artery occlusion balloon greatly reduces the complexity, risk and potential complications of the procedure.

In recent years, a reverse flow protocol having direct surgical access to the common carotid artery CCA (called transcervical or transcarotid access) has been proposed. Transcarotid access greatly shortens the length and tortuosity of the pathway from the vascular access point to the target treatment site thereby easing the time and difficulty of the procedure. Additionally, this access route reduces the risk of emboli generation from navigation of diseased, angulated, or tortuous aortic arch or common carotid artery anatomy.

Thus, the present invention discloses both an improved suturing device that will ease and shorten the procedure as well as a carotid access catheter (e.g., transcarotid access device) introduced into a common carotid artery for treating the same.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

DISCLOSURE OF THE EMBODIMENTS OF THE PRESENT INVENTION

A First Embodiment of the Suturing (Closure) Device

Reference is now made to FIGS. 1*a*-1*j* illustrating the closure device 100, according to one embodiment of the present invention. It is noted that the closure device 100 is used wither along with, before or post the medical procedure performed in the blood vessel (e.g., arteries and veins; more specifically, carotid artery).

According to this embodiment, the closure device 100 comprises a proximal end (not shown in the figs.; maintained outside the blood vessel, 10) and a distal end 11 introduced into the blood vessel (e.g., the carotid) interconnected by body 20.

Also illustrated is a guide wire 12 introduced into the vessel to facilitate in the performance of the required medical procedure.

According to this embodiment, the closure device 100 comprises at least one element, foot fixation element 13, adapted to be closely deployed to the vessel wall to enable passage of the needle (and the sutures) in the desired location within the blood vessel (as will be disclosed hereinafter).

It is further noted that, according to one embodiment of the present invention, the foot fixation element 13 is also in physical communication with the guide wire 12, adapted to fixate the position and/or orientation of the guide wire and to enable the introduction of the suturing means to eventually, post procedure, close the blood vessel.

According to one embodiment of the present invention, the foot fixation element has a blunt edge to prevent any unwanted damage to said blood vessel upon introduction therewithin.

According to another embodiment of the present invention, the foot fixation element is adapted to provide counter force to entry of said at least two pre-shaped hollow tubes, as will be disclosed hereinafter.

Reference is now made to FIG. 1*b*1-1*b*3 illustrating the foot fixation element 13 while being in body 20 of the closure device 100 and introduced into the blood vessel 10.

Furthermore, said Figs. illustrate the deployment of the foot fixation element 13 after the guide wire 12 has been introduced into the blood vessel.

In FIG. 1*b*1, guide wire 12 has been introduced into the blood vessel 10 and the foot fixation element 13 is in the beginning of its deployment into the blood vessel.

In FIG. **1*b*2 the foot fixation element 13** is further introduced into the blood vessel.

In FIG. **1*b*3 the foot fixation element 13 is fully deployed in the blood vessel and engaging with the guide wire 12**.

Reference is now made to FIG. **1*c* illustrating the foot fixation element 13 deployed within the blood vessel 10, substantially perpendicular to the main longitudinal axis of body 20 and engaging with the guide wire 12**.

Full deployment of the foot fixation element 13 is enabled by rotation of the same about axis 19 (see FIG. **1*d***).

According to this embodiment, the foot fixation element 13 comprises at least one groove 15, therewithin guide wire 12 can be accommodated.

According to a preferred embodiment of the present invention, for ease of deployment of the suturing means (as will be disclosed hereinafter), the foot fixation element 13 engages with the guidewire and maintains the same in a predetermined orientation, by means of said at least one groove 15.

Next, the foot fixation element 13 is positioned against the blood vessel wall, see FIG. **1*d***.

The following disclosure relates to the deployment of the suturing elements. According to one embodiment of the present invention, the closure device 100 comprises at least one pre-shaped hollow channel; preferable two pre-shaped hollow channels, each of which have a distal most end, adapted to be deployed within blood vessel 10, and a proximal end being substantially near the proximal end of the suturing device 100.

According to one embodiment, each of the pre-shaped hollow channels is characterized by at least two configurations:

(a) a first configuration, in which each of the pre-shaped hollow channels confined within the closure device 100 and having substantially the same shape as the body 20 of the closure device 100 (namely, straight); and, (b) a second configuration, in which the each of the pre-shaped hollow channels is protruding out of the closure device 100 and having a curved shape (so as to engage, once fully deployed, as will be disclosed hereinafter).

According to one embodiment, deployment of said two channels within blood vessel 10 results in the distal end of the two pre-shaped hollow channels engaging with each other. According to one embodiment of the present invention, the engagement of the distal ends of the channels results in physical contact of the same, such that a single continuous channel is performed by the engagement of the same. It is further within the scope of the present invention where the suture will be introduced therewithin said single continuous channel to eventually (post procedure) close the blood vessel.

According to one embodiment, the distal end of each channel will comprise a magnetic end to ease and ensure the engagement between the two distal ends of the channels.

Reference is now made to FIG. **1*e* illustrating the two pre-shaped hollow channels 16, within the body 20 of closure device 100**.

Reference is now made to FIG. **1*f* illustrating the two pre-shaped hollow channels 16, pierce blood vessel's 10 wall and beginning it deployment therewithin. As can be appreciated from the figures, the hollow channels 16 are pre-shaped to enable the engagement of the distal ends 17** of the two channels. It should be noted that the engagement of the distal ends of the channels refers to physical contact and substantial alignment between the same to result in a single continuous channel throughout which the suture will be passed.

Reference is now made to FIG. **1*g* illustrating full deployment of the channels resulting in engagement of the distal ends of the channels (illustrated as numerical reference 17). Also seen in the fig. is the foot fixation element 13 and guide wire 12. As can be seen, the foot fixation element 13 ensures that the pre-shaped channels 16 and the guide wire 12** are not crossing and 'disturbing' one another.

Reference is now made to FIGS. **1*h*1-1*h*2 illustrating one embodiment of the present invention. According to which each of the distal ends 17 of the channels comprises a magnetic element 18** adapted to enable a magnetic attraction between the two ends and to result in engagement between the channels (namely, mechanical communication therebetween).

Reference is now made to FIGS. **1*j*1 and 1*j*2 illustrating another embodiment of the present invention. According to which at least one of the distal ends 17 of the channels 16 are shaped so as to ease the engagement of between the two channels. According to this embodiment, one of the channel's distal end 17*a* could be cone-shaped so as to better facilitate the mechanical engagement of the two distal ends 17**.

Figure 2:
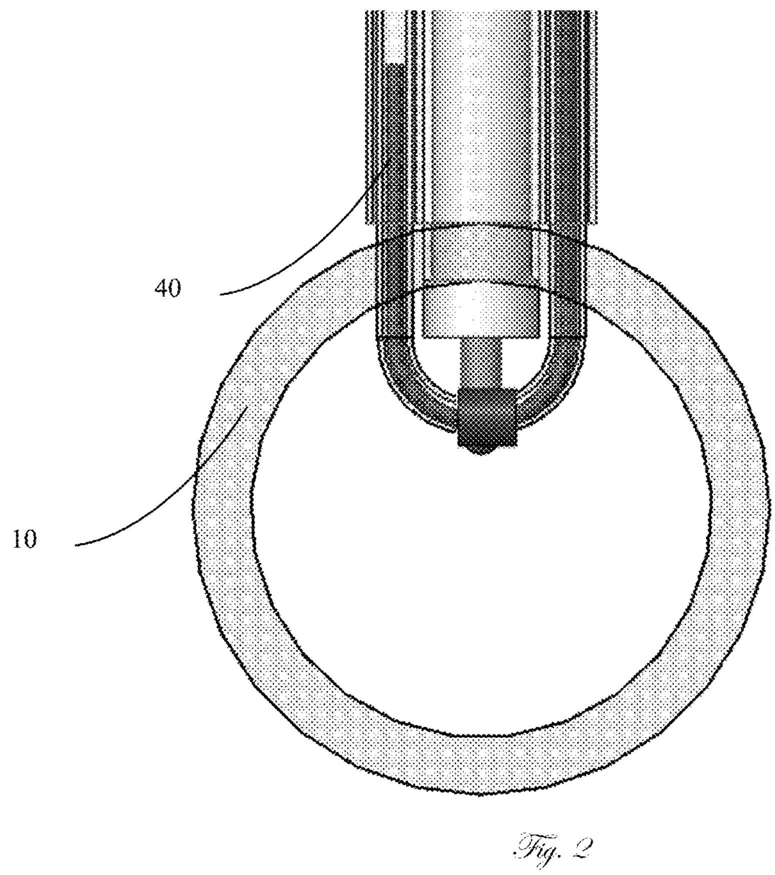
FIGS. 2-3C illustrate the suturing according to one embodiment of the present invention.

FIG. **1*j*1 illustrates a frontal view of the distal end of channels 16 being cone shaped; and FIG. 1*j*2** illustrates a side view of the same.

It should be noted that it is within the scope of the present invention where one of the channels would have a smaller cross-sectional area than the second channel, such that the distal end of the smaller cross sectional area channel could be introduced into the distal end of the second channel.

According to another embodiment, at least one of the distal ends 17 of the pre-shaped channels 16 comprises mechanical mechanism (e.g., clips, one end is flared and the other is introduced inside it) to secure the engagement between the channels.

According to one embodiment of the present invention, at least one of said pre-shaped channels is characterized by a cross sectional area being at least one selected from a group consisting of circular, oval, rectangular, triangular and any combination thereof.

Reference is now made to FIG. **1*i*1 illustrating a cross sectional view of blood vessel 10 with the foot fixation element 13, guidewire 12 and the pre-shaped channels 16** fully deployed.

Finally, when suturing is needed, needle 30 coupled to a suture 40 is advanced through the first channel from the proximal end therefrom to the distal end 17; and, therefrom to the distal end of the second channel and finally to the proximal end of the second channel and out.

Reference is now made to FIG. **1*i*2 illustrating the needle 30 and the suture 40 while the needle 30 is in the first pre-shaped channel 16*a* before passing to the second pre-shaped channel 16*b***.

Reference is now made to FIG. **1*i*3 illustrating the needle 30 and the suture 40 while the needle 30 has passed from the first pre-shaped channel 16*a* into the second pre-shaped channel 16*b***.

Thus, the outcome thereof is the provision of a suture 40 passed through the blood vessel 10 wall (see FIG. 2). It should be noted that the threading could be provided once the medical procedure in the blood vessel is finalized; or, alternatively, before such medical procedure is performed, based on the physician and the medical requirements. Thus, it is within the scope of the present invention where the threading of the suture is passed before or after the medical procedure and the closing (suturing) is performed only at the end of the procedure.

Figure 3A:
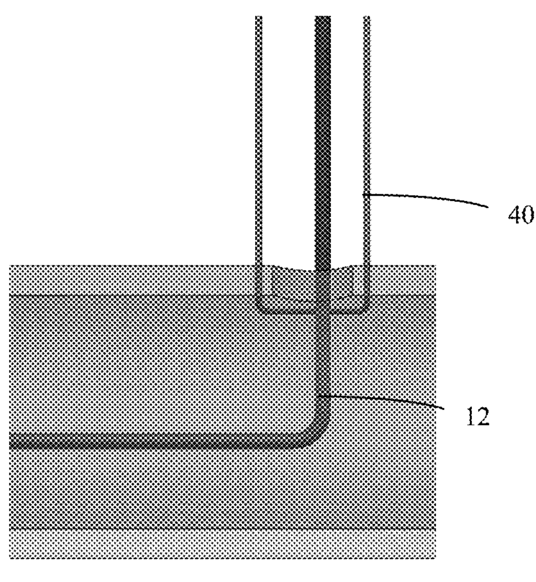
Figure 3B:
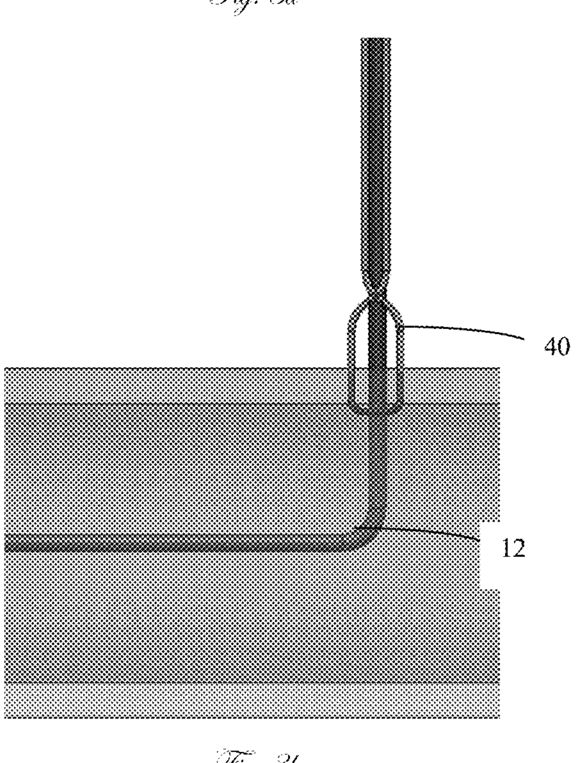
Figure 3C:
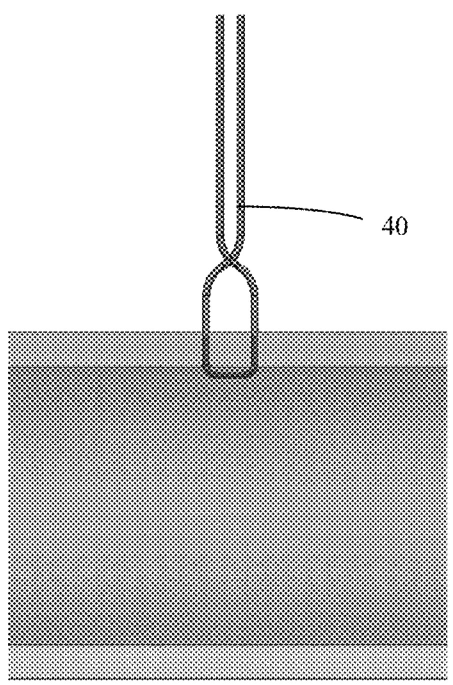

Reference is now made to FIGS. 3*a*-3*c* illustrating the final stage of closing (suturing) the blood vessel 10 by knotting the suture.

When hemostasis is required, the physician secures a knot using the suture (over guide wire 12), see FIG. 3*b*. Finally, the guide wire is removed (see FIG. 3*c*).

Figure 3D:
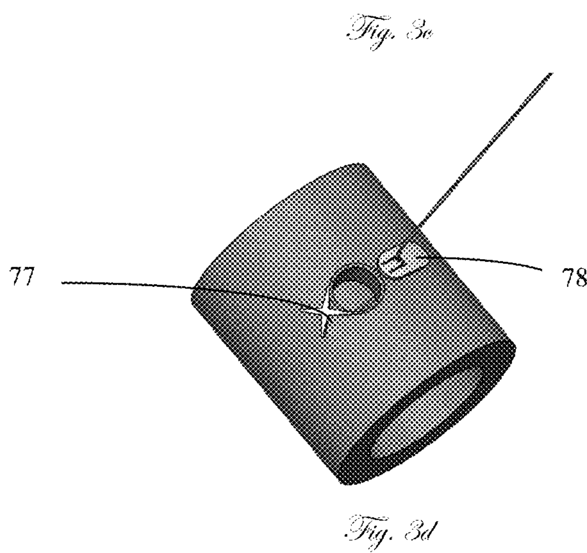
Figure 3E:
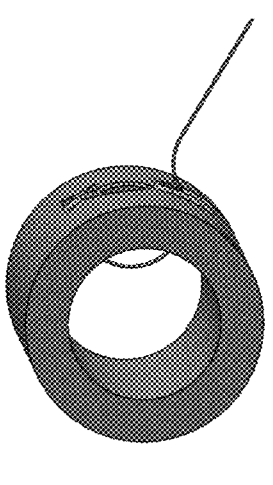

It should be noted that there are other ways known in the literature to secure the fixation of the sutures. E.g., by anchors or ratchet mechanism. In such an embodiment, proximal end of the suture comprises anchors (and/or ratchet) that will be fixated on the blood vessel's 10 wall. Reference is now made to FIGS. 3*d* and 3*e*, illustrating such an embodiment where anchors 77 and ratchets 78 as fixation of the suture to the blood vessel's wall is provided.

According to another embodiment of the present invention the deployment of the pre-shaped channels 16 would be done automatically in one single move (e.g., by a single press of a button in the handle) or manually, by the physician, in a plurality of step-wise movements (e.g., by rotating a knob in the handle until the physician reached it desire deployment; namely, until engagement between the distal ends of the two channels).

Once the pre-shaped channels 16 are deployed and the suture is passed through the two pre-shaped channels 16, the pre-shaped channels 16 are disengaged from one another and retracted back to the proximal end of the closure device, outside the blood vessel and outside the body.

According to another embodiment, the procedure is performed under ultrasound supervision.

According to another embodiment, at least one of said at least two pre-shaped hollow tubes are characterized by a rough surface to facilitate enhance imaging. In case ultrasound is used, such rough surface will enable acoustic reflection.

According to another embodiment, the device additionally comprising at least one sensor adapted to at least one selected from a group selected from (a) engagement of said at least two pre-shaped hollow tubes; (b) disengagement of said at least two pre-shaped hollow tubes; (c) any combination thereof.

A Second Embodiment of the Suturing (Closure) Device

Reference is now made to FIGS. 4*a*-4*d* illustrating another embodiment of the closure device 100, according to one embodiment of the present invention.

As noted above, the closure device 200 is used wither along with, before or post the medical procedure performed in the blood vessel (e.g., arteries and veins; more specifically, carotid artery).

According to this embodiment, the closure device 200 comprises a proximal end (not shown in the figs.; maintained outside the blood vessel, 10) and a distal end 11 introduced into the blood vessel (e.g., the carotid) interconnected by main sheath 20.

According to this embodiment, the closure device 200 comprises at least one alignment element 23, adapted to facilitate alignment between the two pre-shaped hollow channels 16, when the same are deployed within the blood vessel (as disclosed hereinabove).

According to one embodiment of the present invention, the alignment element 23 comprises at least one groove 24 (arc/curved-shaped) adapted to at least partially house the distal ends 17 of the two pre-shaped hollow channels 16 (thereby ensuring engagement/physical contact therebetween).

According to one embodiment of the present invention, the alignment element 23 has a blunt edge to prevent any unwanted damage to said blood vessel upon introduction therewithin.

As disclosed with respect to the first embodiment, the closure device 200 comprises at least one pre-shaped hollow channel; preferable two pre-shaped hollow channels 16, each of which have a distal most end 27, adapted to be deployed within blood vessel 10, and a proximal end being substantially near the proximal end of the suturing device 200.

According to one embodiment, each of the pre-shaped hollow channels is characterized by at least two configurations:

(a) a first (retracted) configuration, in which each of the pre-shaped hollow channels having substantially the same shape as the main sheath 20 of the closure device 200 (namely, straight); and, (b) a second (deployed) configuration, in which the each of the pre-shaped hollow channels is protruding out of the distal end of the closure device 200 and taking a form of a curved shape (so as to engage with each other, once fully deployed, as will be disclosed hereinafter).

According to one embodiment of the present invention, linear movement of each of the channels 16 will convert the same from the first configuration to the second configuration (and vice versa). Thus, pulling the channels 16 towards the proximal end of the device 100 will reconfigure the channels 16 to the first configuration; and, pushing the channels 16 towards the distal end of the device 100 will reconfigure the channels 16 to the second configuration.

According to another embodiment, deployment of said two channels 16 within blood vessel 10 results in the distal end of the two pre-shaped hollow channels engaging with each other. In order to facilitate such an engagement, groove 24 is provided in alignment element 23, as illustrated in FIG. 4*b* and a closer view in FIG. 4*c*.

According to another embodiment, when needed, said two channels 16 are introduced (namely, by linearly moving the same distally into blood vessel).

Figure 4A:
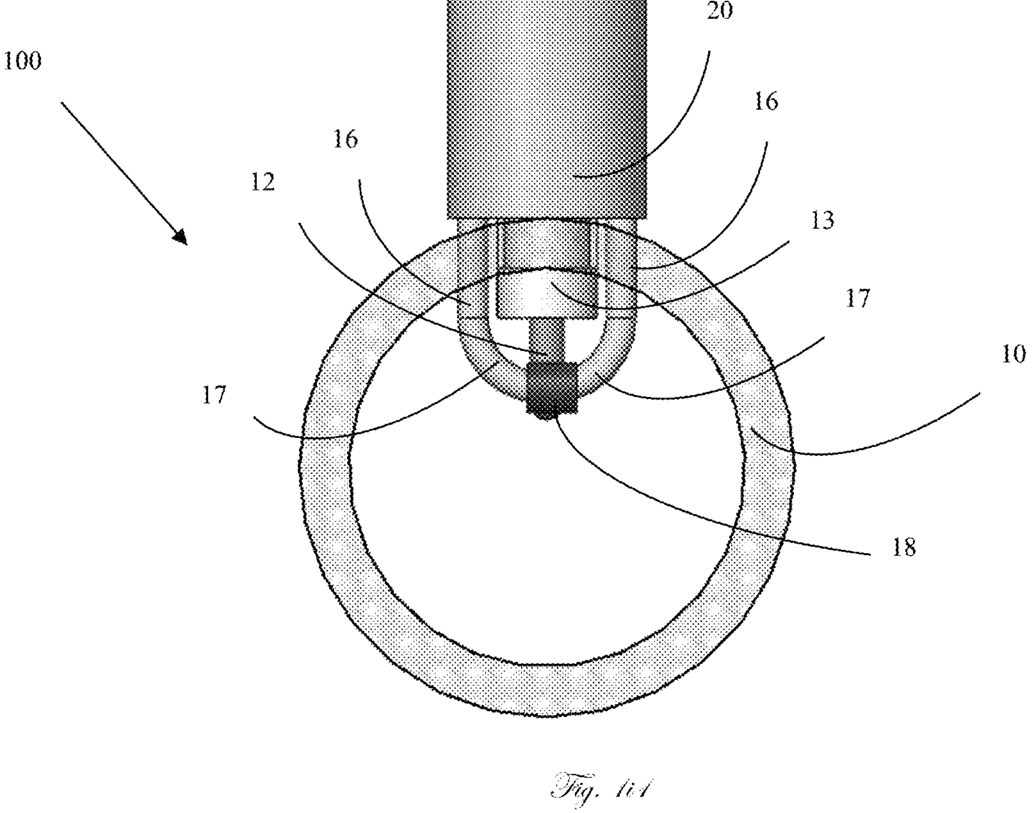
Figures 4A, 4B:
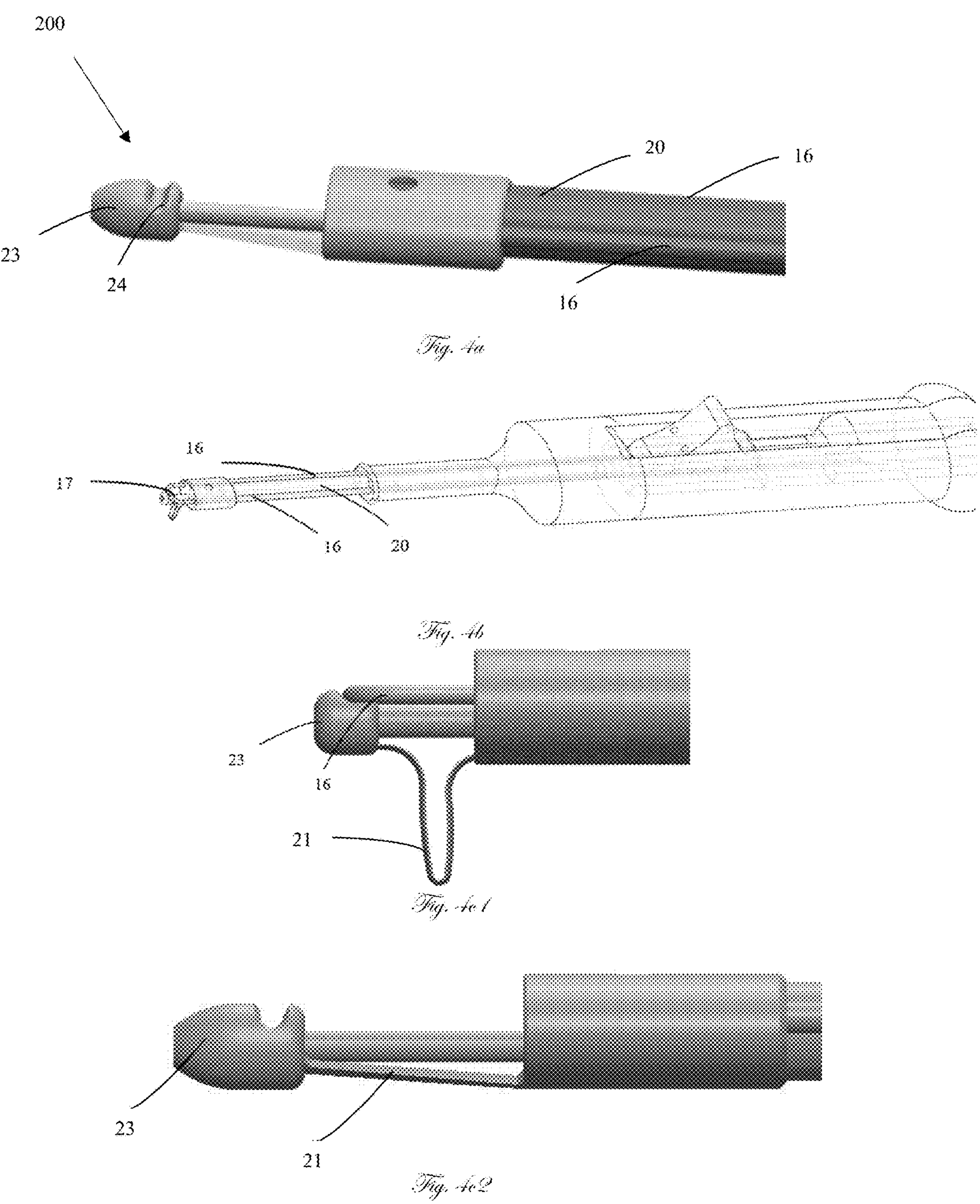

As seen in FIGS. 4*a*-4*b*, and according to one embodiment, two channels 16 are positioned externally to the main sheath 20.

It should be noted that it is within the scope of the present invention where the two channels 16 are positioned internally to the main sheath 20.

Engagement of the distal ends of the channels: According to one embodiment of the present invention, the engagement of the distal ends of the channels results in physical contact of the same, such that a single continuous channel is performed by the engagement of the same. It is further within the scope of the present invention where the suture will be introduced therewithin said single continuous channel to eventually (post procedure) close the blood vessel.

According to one embodiment, the distal end of each channel will comprise a magnetic end to ease and ensure the engagement between the two distal ends of the channels.

Such magnetic end enables a magnetic attraction between the two ends and to result in engagement between the channels (namely, mechanical communication therebetween).

According to another embodiment, at least one of the distal ends 17 of the channels 16 are shaped so as to ease the engagement of between the two channels. According to this embodiment, one of the channel's distal end 17*a* could be cone-shaped so as to better facilitate the mechanical engagement of the two distal ends 17.

It should be noted that it is within the scope of the present invention where one of the channels would have a smaller cross-sectional area than the second channel, such that the distal end of the smaller cross sectional area channel could be introduced into the distal end of the second channel.

According to another embodiment, at least one of the distal ends 17 of the pre-shaped channels 16 comprises mechanical mechanism (e.g., clips, one end is flared and the other is introduced inside it) to secure the engagement between the channels.

According to one embodiment of the present invention, at least one of said pre-shaped channels is characterized by a cross sectional area being at least one selected from a group consisting of circular, oval, rectangular, triangular and any combination thereof.

Reference is now made to FIGS. 4*c*1-4*c*2, illustrating another embodiment of the present invention. According to which, a bendable anchoring support element is provided, 21. According to this embodiment, element 21 provides counter force against the vessel wall. Element 21 has positions, an initial position where the same is substantially straight and parallel to the vessel's longitudinal axis (see FIG. 4*c*1), and a second position where element 21 is bendable enabling counter force against the blood vessel's wall (see FIG. 4*c*2).

Reference is now made to FIGS. 4*d*1 and 4*d*2 illustrating another embodiment of the present invention. According to which, two lumens 161 are fixedly provided externally to the main sheath 20 therewithin the channels 16 are introduced into the blood vessel.

Said lumens 161 are characterized by a proximal end positioned in the closure device proximal end and a distal end positioned in the closure device distal end, interconnected by a main longitudinal axis.

Thus, when needed, the channels 16 are introduced into lumens 161 from the proximal end and exit through the distal end thereof (to be reconfigured to their second (deployed) configuration.

A Third Embodiment—One Pre-Shaped Form Tube

Figure 5A:
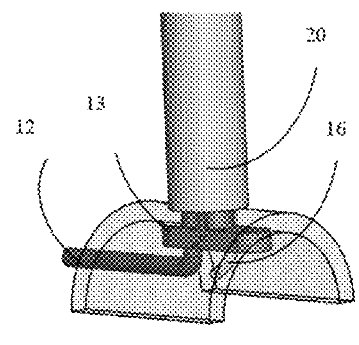
FIGS. 5A-5B illustrate a third embodiment of the present invention.
Figure 5B:
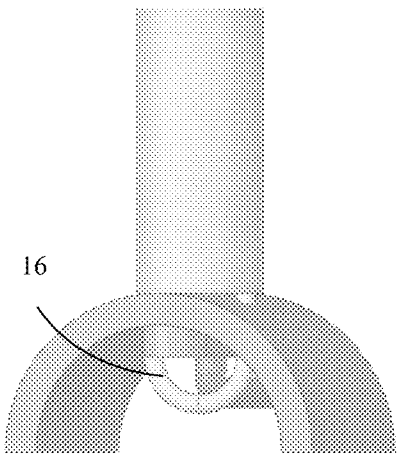
Figure 6A:
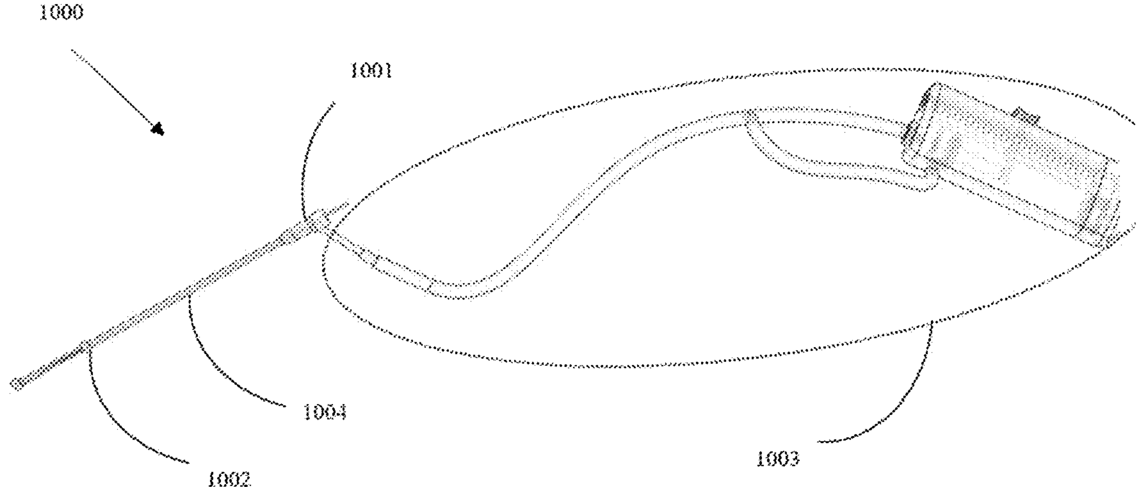

Reference is now made to FIGS. 5*a*-5*b*, illustrating a third embodiment of the present invention, in which only one pre-shaped tube 16 is employed.

According to this embodiment, the closure device comprising only one pre-shaped hollow tube 16 having a proximal end, substantially at said proximal end of said closure device and a distal end, adapted to be introduced from said distal end of said closure device into the blood vessel at a predetermined first location; wherein upon deployment of said pre-shaped hollow tube 16 out of said closure device, within the blood vessel, said distal end thereof is adapted to assume said pre-shape form and exit said blood vessel, at predetermined second location, back into said closure device and the proximal end thereof, and to enable a suture, being threaded through said pre-shaped hollow tube at said at predetermined first location, to be extracted from the artery at said at predetermined second location.

According to one embodiment, the pre-shape form is a U-shape.

Reference is now made to FIG. 5*a* which illustrates the initial deployment of the pre-shaped hollow tube 16 out of said distal end of the closure device.

Reference is now made to FIG. 5*b* which illustrates the full deployment of the pre-shaped hollow tube 16 out of said distal end of the closure device. Namely, the re-entry of the pre-shaped hollow tube 16 into the closure device.

It should be noted that all features disclosed with respect to the first embodiment are applicable to the second embodiment as well.

The Vascular Access Catheter

As described above, according to one embodiment of the present invention, the vascular catheter is used for carotid artery intervention.

According to another embodiments, it can be used in a percutaneous endovascular/neurovascular interventional method and which may be used to perform vascular surgery at and from various sites. For example, the catheter may be used to perform vascular surgery within, or gain access via, the brachial, femoral, carotid, radial, ulnar, axillary or other blood vessels.

According to a more specific example, the catheter may be used to access the carotid artery for internal or common carotid artery stenosis. More specifically, the catheter of the present invention is primarily designed for percutaneous cervical access to the carotid artery for neurovascular intervention.

It is further within the scope of the present invention, where at least one selected from a group consisting of percutaneous vascular surgical device, transcarotid access device, introduced into a common carotid artery for treating the same.

However, it should be noted that it is within the scope of the present invention, where the catheter can be used for surgical procedures such as angioplasty, stenting, clot retrieval for stroke or heart attack, embolic protection, stroke prevention, brain aneurysm embolization, uterine embolization, angiodysplasia embolization in the bowel for bleeding, varicocele embolization, tumour embolization, visceral aneurysm embolization and any other suitable procedures.

As disclosed above, one object of the present invention is to treat carotid artery diseases and specifically during CAS. More specifically, the present invention discloses a percutaneous transcarotid access catheter for use during direct surgical access to the common carotid artery CCA (transcarotid access).

According to one embodiment of the present invention, the transcarotid access catheter (refers hereinafter as 'catheter') will comprise the closure device as described above; according to another embodiment, the closure device will be provided separately from the transcarotid access catheter and will be used either prior to the carotid stenting or thereafter.

As noted above, the catheter of the present invention is provided for treating carotid stenosis or other vascular issues. Such a procedure includes temporarily block the carotid or other artery or vessel in order to stop ante grade blood flow during the surgical procedure and encourage retrograde reverse flow to enhance brain perfusion, the removal of emboli which could otherwise cause a stroke, the deployment of a stent through the catheter for treatment of carotid artery disease, and the closure of the artery on completion of the operation.

According to one embodiment of the present invention, the catheter is made to be fully rigid, partially or fully flexible in the longitudinal direction, or may be locally flexible in order to allow deformation during insertion of the same.

Such a construction will allow a proper cannulation of the carotid artery, with suitable angulation of the same, allowing the catheter to access the carotid artery by means of percutaneous entry from a position on the neck of the patient, significantly reducing the length of artery to be traversed in order to reach the surgical site, thereby reducing surgery times and risk of embolization.

Reference is now made to FIG. 6*a*-7*b* illustrating an embodiment of the vascular catheter 10000 according to the present invention.

According to one embodiment, the catheter 1000 comprises a proximal end 1001, maintained outside the patient; and, a distal end 1002 percutaneous introduced into the carotid; the distal end and the proximal end of the catheter are interconnected by a body 1004 (also referred to as main sheath).

As will be disclosed hereinbelow, the catheter also comprises a reverse flow means 1003. As will be disclosed below such reverse flow means could be provided by e.g., a simple automatic/semi-automatic or manual syringe. The reverse flow could be achieved automatically in one single move (e.g., by a single press of a button in the handle) or manually, by the physician, in a steps-wise manner.

Reference is now made to FIG. 6*b*1 providing a closer view of the distal end 1002 of the catheter 1000 (when in used during the carotid intervention).

As will be disclosed hereinbelow, catheter 1000 comprises at least 3 inflatable elements (namely, balloons):

(a) at least one first inflatable element 1005 (referred to as balloon 1005), positioned at the end of the distal sheath 1004, adapted to, as will be described herein below, be inflated and to occlude/block the flow in the common carotid artery;

(b) at least one second inflatable element 1006 (referred to as balloon 1006), adapted to, as will be described herein below, occlude/block the flow in the e.g., the external carotid artery; and, (c) at least one third inflatable element 1007 (referred to as balloon 1007), adapted to, as will be described herein below, occlude/block the flow in the e.g., the internal carotid artery.

According to one embodiment of the present invention each of the balloons are disposed at a distal end of a guide wire 1008.

It is emphasized that each of the inflatable elements is in fluid communication with the proximal end 1001 of the catheter, so as each could be inflated by pumping a fluid such as a saline solution or other solution, or air/carbon di-oxide. Furthermore, each balloon is provided with specific\dedicated channel within body/main sheath 1004 such that fully inflating one of which does not preclude inflating another one.

Reference is now made to FIG. 6*b*2 illustrating a cross section view of the distal end 1002. As seen in the figure, the channels 16 (the throughout which the suture for closing the carotid is passed) is externally positioned to main sheath 1004 (which is the working channel throughout which the guide wire/balloons and inflation/deflation thereof/stent(s) etc. introduced).

According to one embodiment of the present invention, at least one of the inflatable elements is formed from any suitable biocompatible material.

According to another embodiment, at least one of the inflatable elements includes at least one marker, adapted to facilitate visualization of the positioning of the same, under a fluoroscope during the various stages of the surgical procedure. According to one embodiment of the present invention said at least one marker is a radiopaque marker.

Referring back to the figure, the catheter comprises at least one first balloon 1005 being in fluid communication with the proximal end 1001 of the catheter. Said balloon 1005 can be inflated by pumping a fluid such as a saline solution or other solution, or air/carbon di-oxide. When fully inflated within the common carotid artery the first balloon 1005 is designed to results in total occlusion of the common carotid artery. Thus, the first balloon 1005 has a diameter or size sufficient to allow the same to result, when fully inflated, in endo-clamping, in order to completely occlude the common carotid and therefore prevent blood flow past balloon 1005.

In the same manner, the balloon 1005 may be deflated by withdrawing therefrom. It is within the scope of the present invention where inflation and deflation of at least one of the inflatable elements is at least partially reversible, and in a preferred embodiment. Fully reversible.

As described above, a second inflatable element, balloon, 1006 is provided.

According to one embodiment, said balloon 1006 is provided with at least one radiopaque markers, again to allow the position of the second balloon 1006 to be visualized during the surgical procedure by means of a fluoroscope. Again, it will be understood that any other combination of radiopaque markers, or any other suitable functional alternative to a radiopaque marker may be employed.

As the first balloon 1005, the second balloon 1006 is inflatable via one dedicated lumen out of the lumens within the catheter 1000, through which a fluid such as saline may be pumped at the proximal end 1001 of the catheter 1000. Any suitable source of pressurized fluid may be used.

As described above, a third inflatable element, balloon, 1007 is provided.

According to one embodiment, said balloon 1007 is provided with at least one radiopaque markers, again to allow the position of the third balloon 1007 to be visualized during the surgical procedure by means of a fluoroscope. Again, it will be understood that any other combination of radiopaque markers, or any other suitable functional alternative to a radiopaque marker may be employed.

As with the first balloon 1005, the third balloon 1007 is inflatable via one dedicated lumen out of the lumens within the catheter 1000, through which a fluid such as saline may be pumped at the proximal end 1001 of the catheter 1000. Any suitable source of pressurized fluid may be used.

It should be noted that the distal end 1002 may comprise at least one marker that can be used under the fluoroscope to allow the surgeon to ascertain the position of the distal end relatively to the blood vessel.

The role of each balloon will be disclosed hereinafter.

As disclosed above, the catheter 1000 of the present invention additionally comprises a reverse flow means 1003.

Figure 7A:
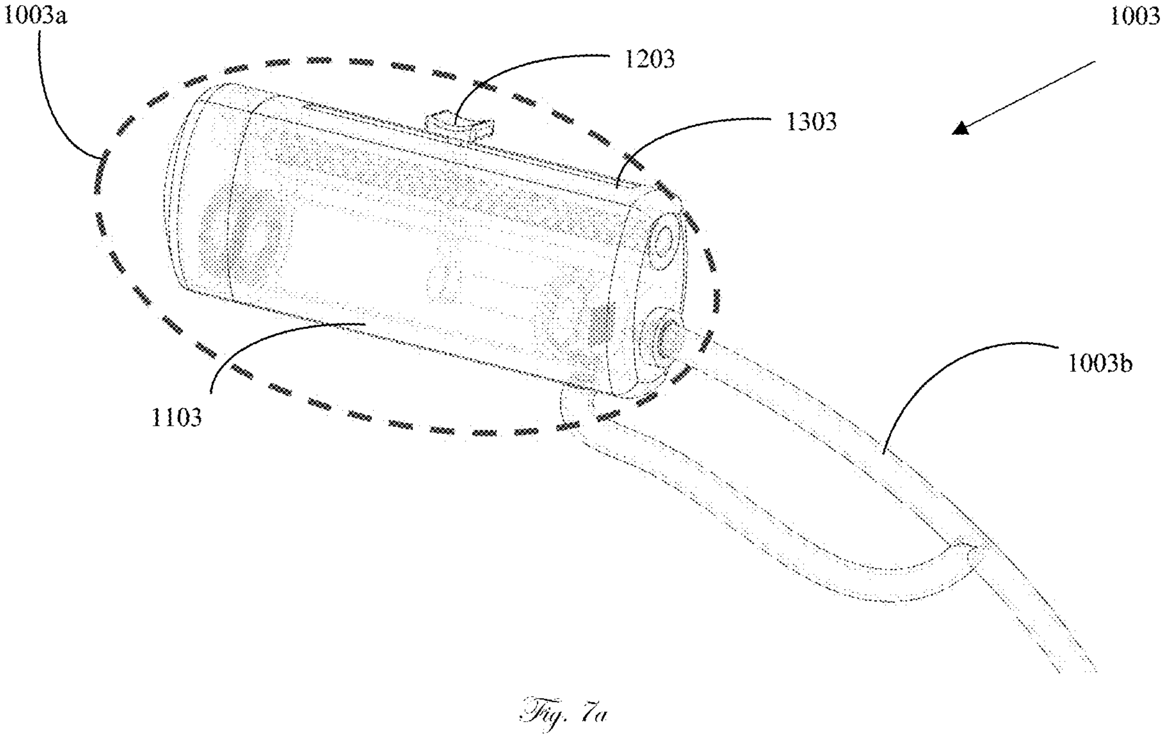
FIGS. 7A-7B illustrate the reverse flow means 1003.
Figure 7B:
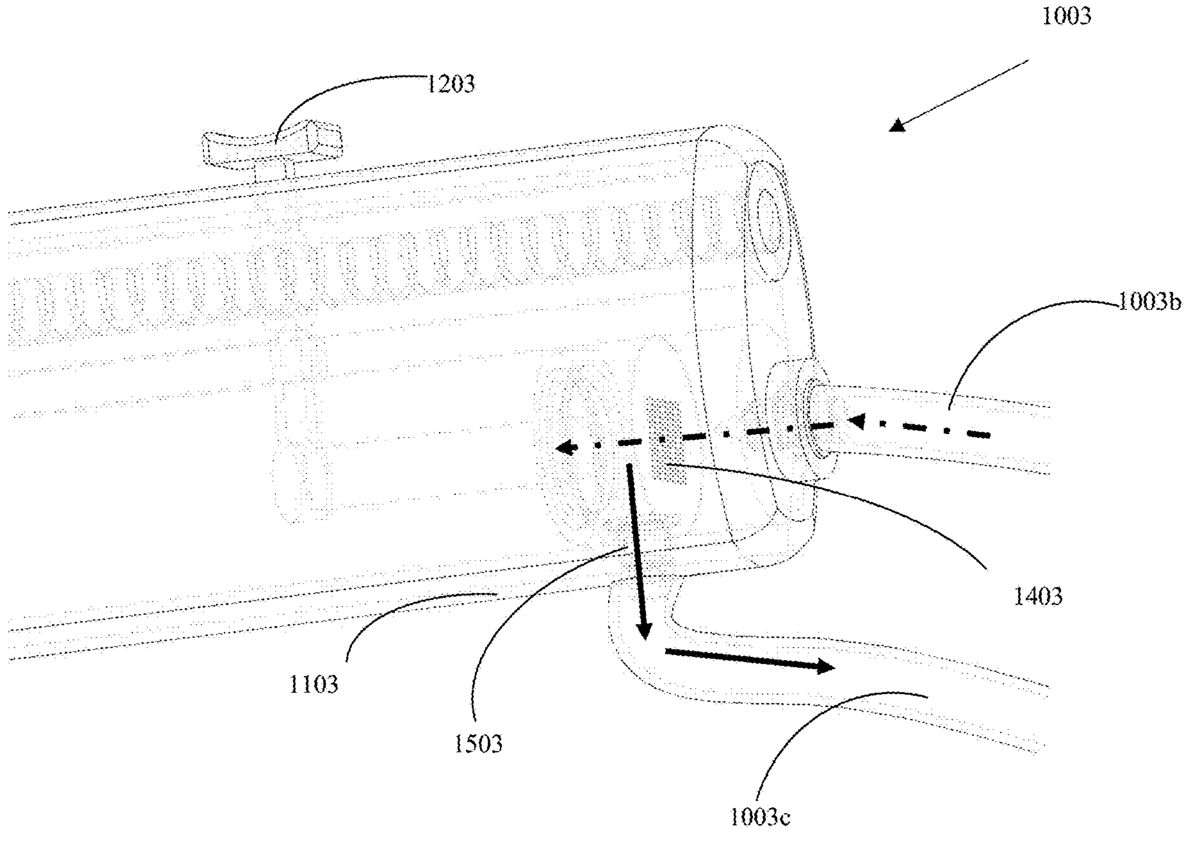

Reference is now made to FIGS. 7*a*-7*b* illustrating the reverse flow means 1003, FIG. 7*b* being a closer view of FIG. 7*a*. According to a preferred embodiment of the present invention the reverse flow means 1003 is a negative pressure generator 1003*a*. One example is a pump or a syringe. According to one embodiment, the syringe is either a full manual syringe, semi automatically or a fully automatic syringe. However, any it is within the scope of the present invention that any negative pressure (and essentially suction application means) are within the scope of the present invention. According to another embodiment, pressure of 0-50 mmHg is within the scope of the present invention.

As disclosed above, the reverse flow means 1003 are in fluid communication with the proximal end 1001 of catheter 1000. As seen in FIGS. 7*a*-7*b*, at least one tube 1003*b* is provided to fluidly connect the negative pressure generator 1003*a* the proximal end 1001 of catheter 1000 so as to apply reversal flow to e.g., within the carotid artery.

This negative pressure or suction is utilized to establish reverse blood flow in the blood vessel in which surgery is being performed in order to locally withdraw blood and any emboli from about the surgical site (e.g., the carotid artery).

It will be appreciated that any other suitable connection between the negative pressure generator 1003*a* and the proximal end 1001 of catheter 1000 may be provided to establish fluid communication between the same.

It is further within the scope of the present invention where the negative pressure generator 1003*a* can apply sufficiently enough suction pressure to withdraw substantially the required amount of fluid from the artery (e.g., the carotid artery).

According to one embodiment of the present invention, the negative pressure generator 1003*a* comprises a body 1103 and a plunger 1203 which may be reciprocally moved within a dedicated groove 1303 in body 1103, such that movement in one direction generates suction or negative pressure in the interior volume of the body 1103 in any conventional and known methods in the art; and movement in the other direction can facilitate the return of fluids (namely blood) back to the artery (through a dedicated tubing; e.g., 1003*c*, as will be detailed below).

During use of the catheter 1000 this suction or negative pressure will thus be transmitted via proximal end 1001, through body/main sheath 1004 to the distal end 1002 of the catheter 1000.

It should be noted that catheter 1000 is comprise multiple lumens such that it enables the passage of surgical devices (such a guide wires, catheters, stents etc.) while enabling either suction of fluids from the artery.

Furthermore, it is within the scope of the present invention, where the proximal end 1001 being sealed by a suitable valve which provides a fluid tight seal at the proximal end 1001 while permitting the passage of surgical devices such a guide wires, catheters and the like while maintaining said seal.

As noted above, the reversal of blood flow generated by the reverse flow means 1003 draws blood from the blood vessels (e.g., the carotid) in order to facilitate embolic residues removal during the procedure (and thus, provide embolic protection).

According to another embodiment of the present invention the guide wires used are hollow and can facilitate the reversal of blood flow therewithin. In other words, the guide wires can be in fluid communication with the reverse flow means and enables the blood withdraw from the blood vessels therewithin.

According to another embodiment of the present invention, the transcarotid access catheter 1000 will comprise at least one distal filter adapted to capture the embolic particles to prevent passage into the cerebral vasculature.

Due to the significantly shortened access path to the surgical site, in the case of percutaneous access via the neck to the carotid artery, the surgical time is very significantly reduced and as a result only a relatively small quantity of blood is required to be aspirated via the negative pressure generator 1003*a*, and thus the catheter 1000 does not necessarily require reintroduction of the aspirated blood, thereby avoiding the requirement for filtering of the blood and complex additional apparatus to effect reintroduction to the patient. This, again, significantly reduces the operative time, the complexity and cost of the procedure, further improving patient experience over conventional systems.

However, it is within the scope of the present invention, where, is there is a requirement to re-introduce the withdraw blood—a dedicated tube 1003*c* is provided. As described above, once plunger 1203 is move in one direction—suction is applied and blood will be withdrawn from the artery into the body 1103 of reverse flow means 1003 (illustrated in the figure in dotted arrows); moving the plunger to the other direction, will result in the reintroduction of blood into the artery (illustrated in the figure as straight arrows).

According to another embodiment of the present invention, the body 1103 comprise at least one distal filter 1403. Thus, the withdrew blood is filtered before entering the body 1103.

As seen in the figure, should the blood be reintroduced back to the carotid artery, the same travel through a dedicated tube 1103*c* provided with a dedicated valve 1503 operable to be open only upon the requirement to reintroduce the blood.

Manually operable negative pressure generator 1003*a* by means of the plunger 1203 (either automatically operated or semi-automatic operated or manually-operated) allows the surgeon to selectively establish suction and withdraw, as much as needed, blood. Furthermore, when suction is required, the surgeon activate the plunger 1203 or the negative pressure generator 1003*a* for a preselected period of time that suction is required, namely while the surgical procedure is being performed and thus while emboli may be created, and to then close the negative pressure generator 1003*a* once the procedure is complete and the risk of emboli is removed.

The reverse flow means 1003 may additionally comprise indicating means adapted to indicate 'safe time' to perform the procedure. Namely, when blood is still being evacuated from the artery. When no blood and further removed, the indicating means indicate to the surgeon to finalize the procedure.

The indicating means could be visual, auditable, tactile and any combination thereof.

According to one embodiment, once the vascular surgical procedure is completed, the closure device 100 is operable through the catheter 1000 (as an integral part thereof), thereby further simplifying the entire procedure by allowing all of the operations of the entire procedure to be performed with a single catheter 1000.

As seen in FIG. 6*b*, and according to one embodiment, should the closure device 100/200 is operable through the catheter 1000, the closure device 100/200 is positioned externally to the main sheath 1004. In other words, the channels 16 are positioned outside the main sheath 1004.

It should be noted that inflation/deflation of each of the balloons and/or application of the reverse flow means are provided within the main sheath 1004.

According to another embodiment, the closure device 100 is positioned internally to the main sheath 1004.

According to another embodiment, the closure device 100 is used as a standalone means device separately from the catheter 1000.

Figures 8A, 8B, 8C:
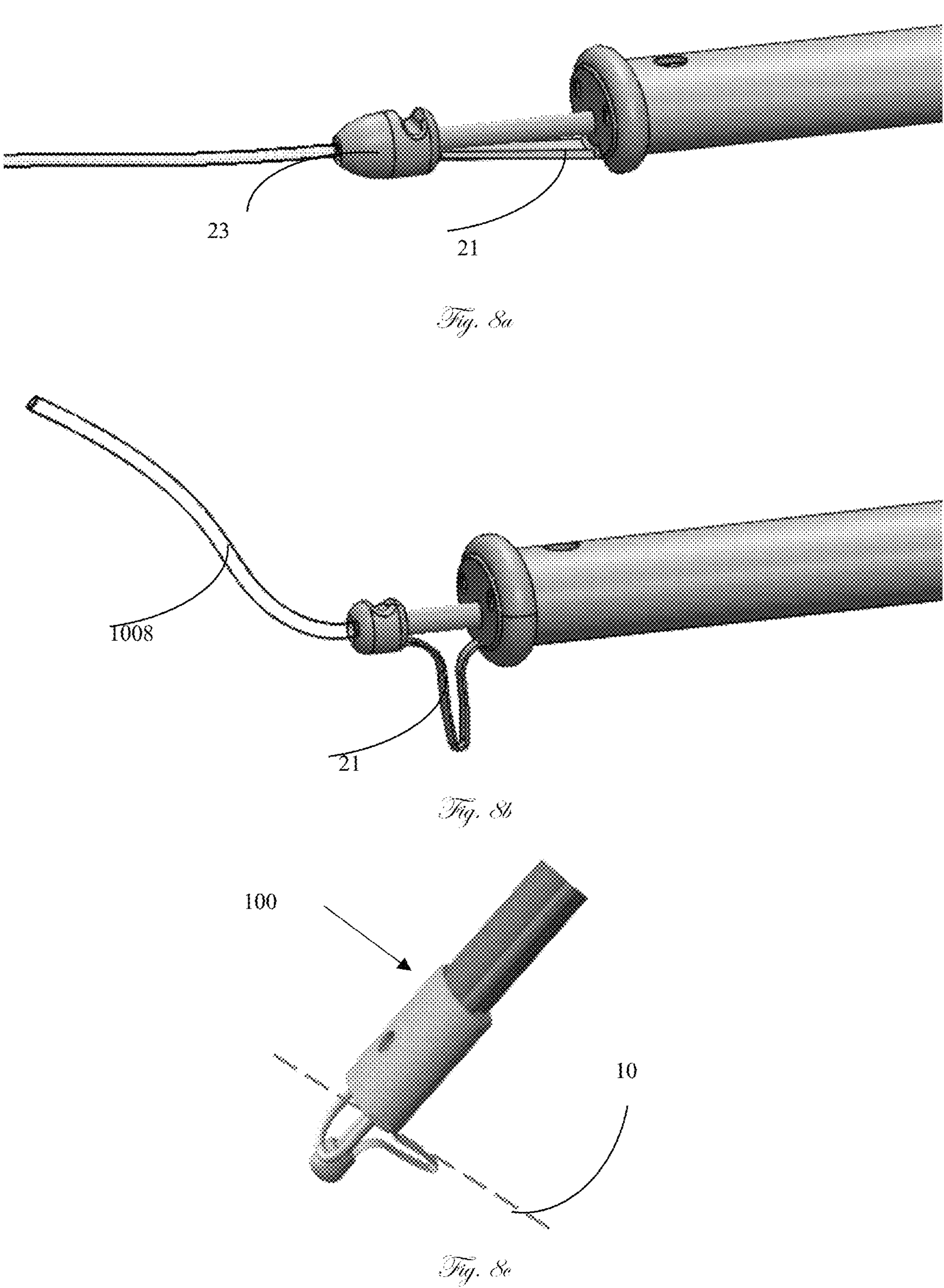
FIGS. 8A-8N illustrate the transcarotid access catheter for the performance of the percutaneous cervical access to the carotid artery for neurovascular intervention.
Figure 8D:
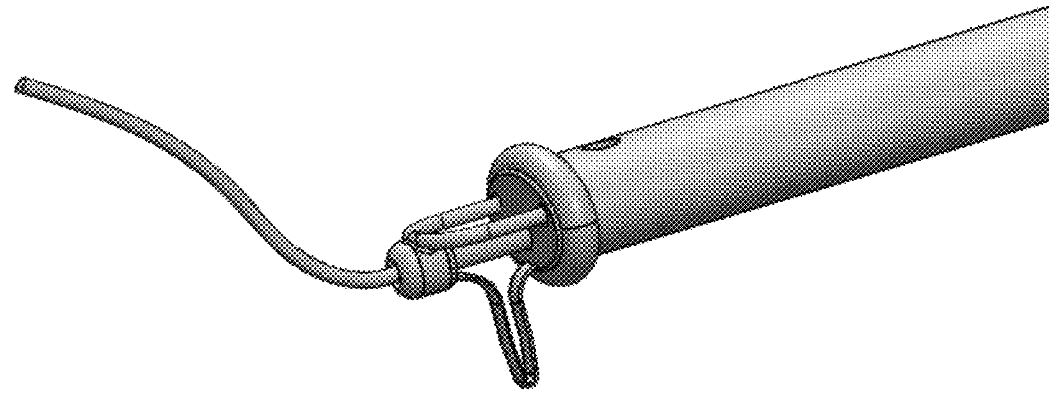
Figure 8E:
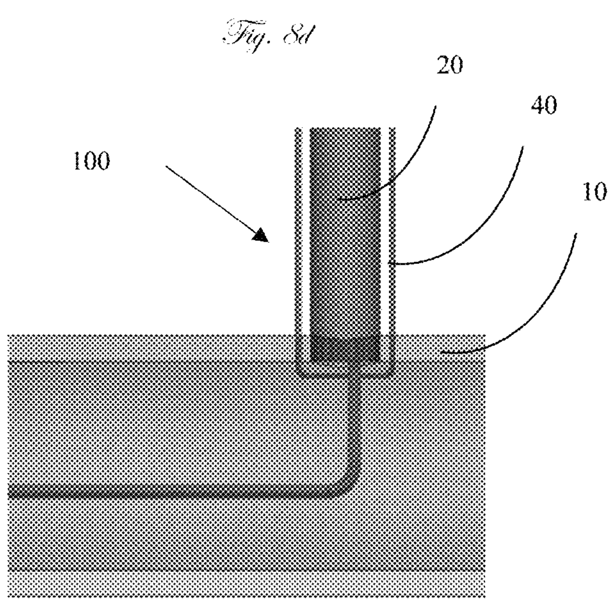
Figures 8F, 8G:
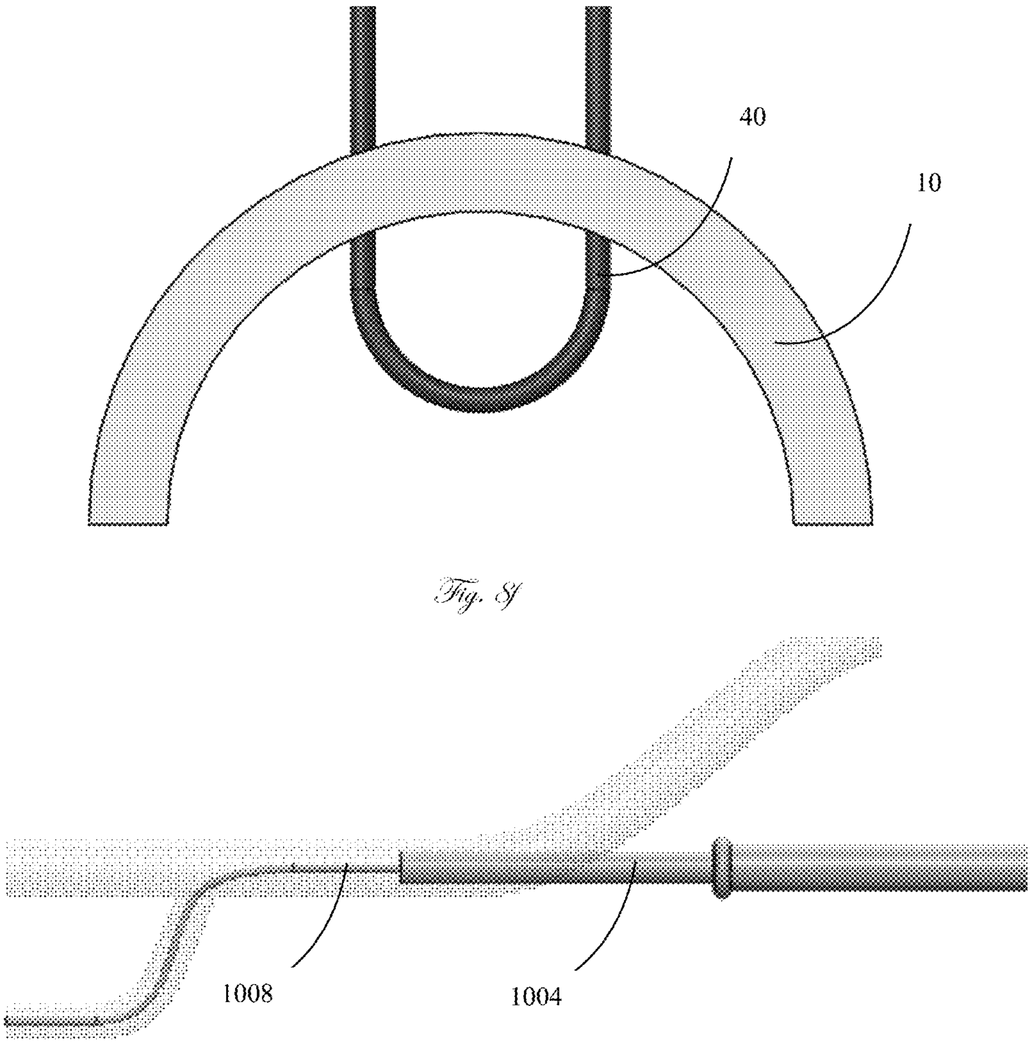

The procedure is performed as follows:

a. In the case stenosis of the carotid artery that required intervention access at the neck is preformed for entering the blood vessel above the clavicle.
b. Next, optionally, engage the closure device 100, as disclosed above. Alternatively, this step will be performed after the end of the procedure (see. If the closure device 100 is activated, the next step is disengaging the closure mechanism and withdrawing the two pre-shaped hollow channels (see FIGS. 8*a*-8*d*, where in 8*a* alignment element 23, adapted to facilitate alignment between the two pre-shaped hollow channels 16 is positioned and element 21 is stretched; in FIGS. 8*b*-8*c* element 21 is bent and provides counter force against the vessel wall 10; in FIG. 8*d* channels 16 are introduced and engage with alignment element 23; in FIG. 8*e* the suture had been threaded through the channels 16; In FIG. 8*f* suture 40 is shown threaded through the vessel 10).

c. One the suture has been threaded the closure device is extracted and the guide wires (disposed with the inflatable elements on the distal end thereof) are introduced through the main lumen (see FIG. 8*g*). Next, the first balloon 1005 is independently inflated, either by the introduction of a saline solution other fluid, thereby inflating the first balloon 1005 to block the common carotid artery and thus occlude blood flow during the stenting or other surgical procedure. The location of the first balloon 1005 immediately adjacent the distal end 1002 of the catheter 1000 allows the common carotid to be completely occluded while leaving the distal end 1002 open and thus enabling introduction of further tools (as will be discussed hereinafter) through the distal end 1002. The location and amount of inflation can be provided to the surgeon by means of at least one marker visualized by imaging means.

Figure 8H:
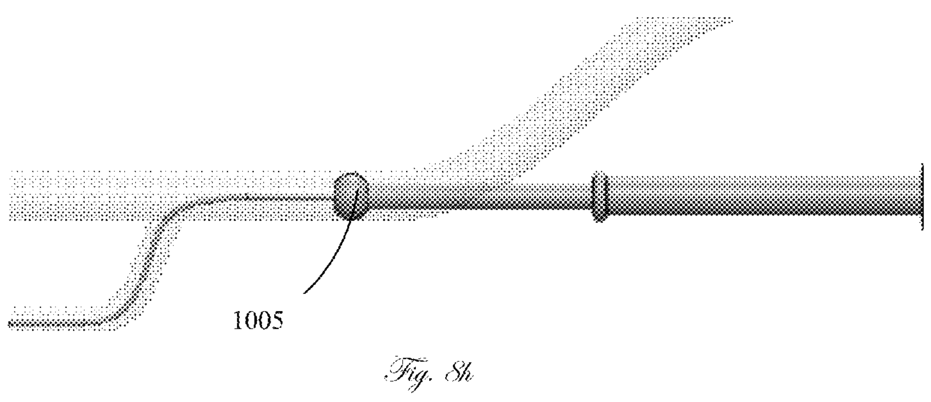
Figure 8I:
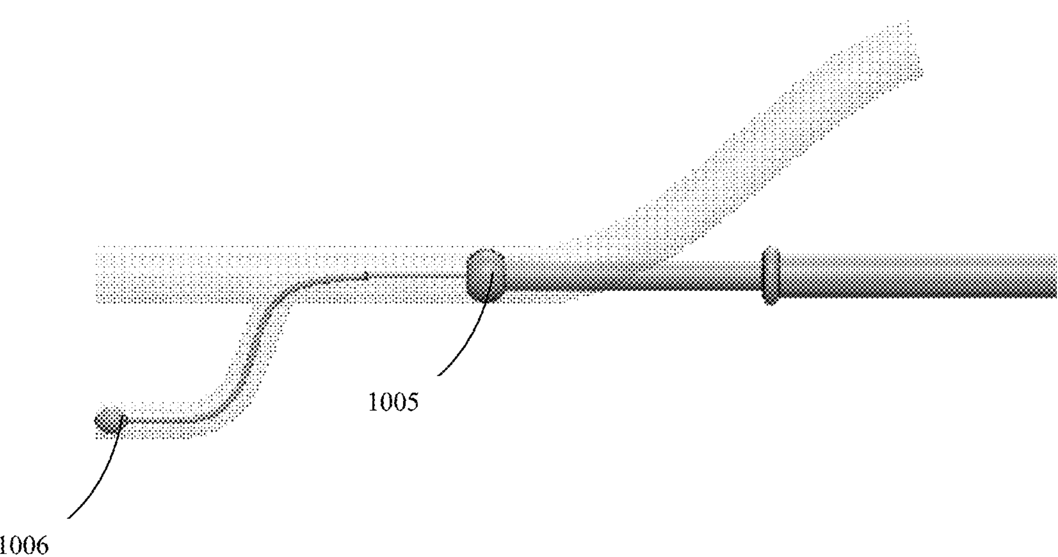
Figure 8J:
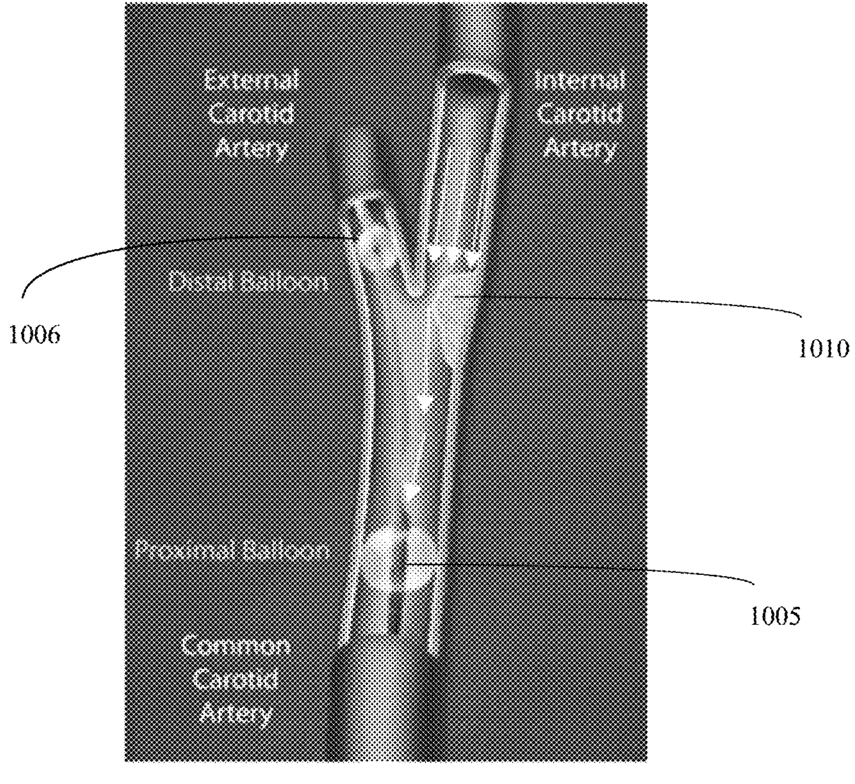
Figure 8K:
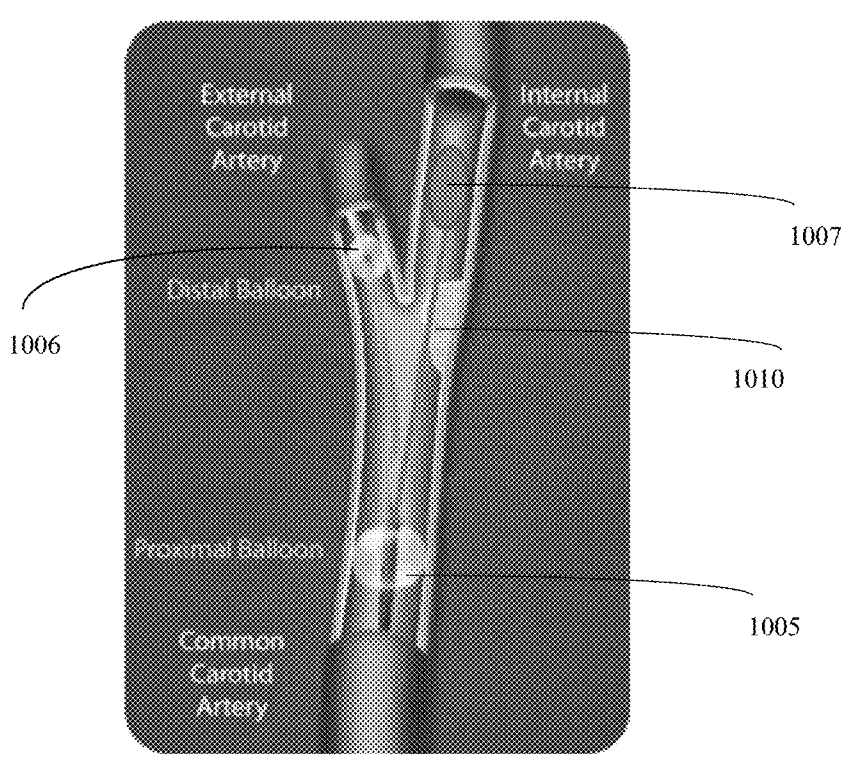
Figure 8L:
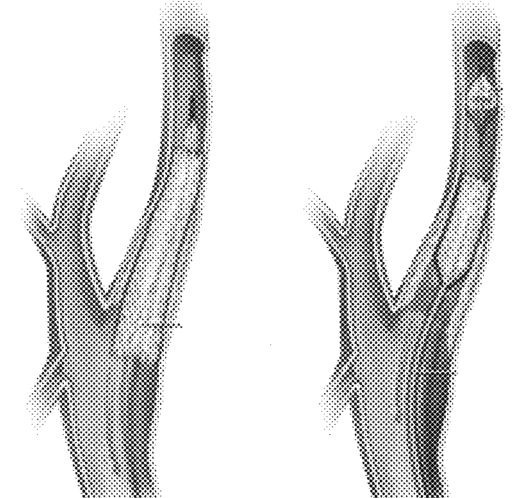
Figure 8M:
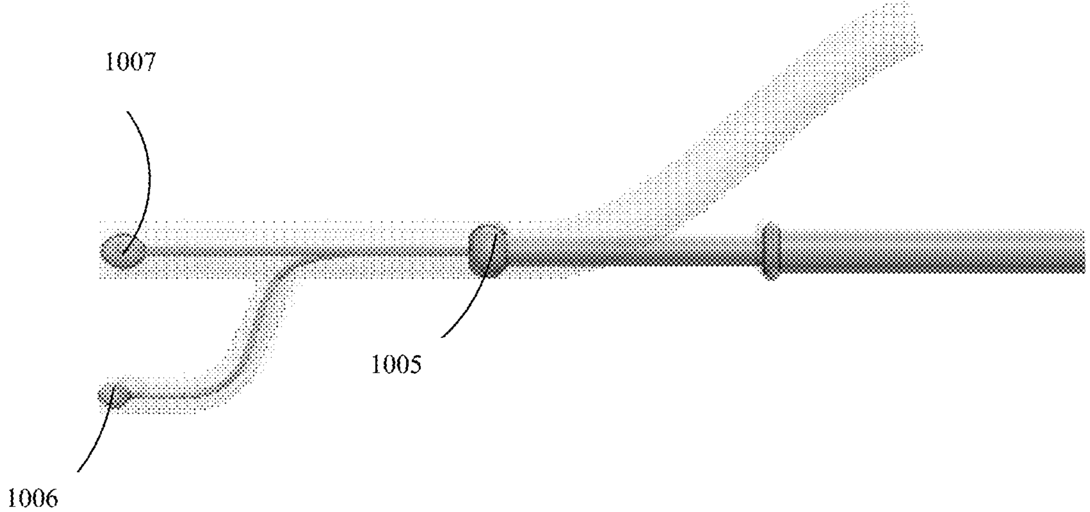

According to one embodiment, at least one marker provided with said balloon is used under the fluoroscope to allow the surgeon to ascertain that the entire length of the first balloon inserted into the blood vessel before continuing with the surgical procedure; ascertain the amount of balloon inflated so as to ensure the balloon seal-tight occlude the vessel (see FIG. 8*h*).

d. Next, a guide wire is inserted into the blood vessel and is advanced to the site at which the surgical procedure is to be performed, in this case a partial blockage 1010 of the carotid artery. The guide wire is thus advanced through and slightly past the blockage in order to facilitate the insertion of a stent in conventional fashion.

e. Next, the second balloon 1006 is independently inflated (either in the external carotid artery or in the internal carotid artery, depending where the blockage is; namely, if the blockage is in the external carotid artery, the second balloon 1006 is inflated in the internal carotid artery and vice versa), either by the introduction of a saline solution other fluid, thereby inflating the second balloon 1006 to block either the external carotid artery or the internal carotid artery, as discussed above. The location and amount of inflation can be provided to the surgeon by means of at least one marker visualized by imaging means (see, again, FIG. 8*i*).

f. Next, the reverse flow means 1003 is activated. For example, the plunger 1203 is moved (either manually, automatic or semi-automatic) in a predetermined direction in groove 1303 in body 1103 in order to generate negative pressure or partial vacuum within the vessel (essentially below 50 mmHg); and, thus establish retrograde flow from the vessel into body 1103 of the reverse flow means 1003 in order to effect the removal of blood from around the surgical site, which will thus carry away any emboli generated by the introduction and deployment of the stent or other device at the site of the blockage. In other words, the activation of the reverse flow means 1003 effect aspiration of the blood while also avoiding brain hypoperfusion (see FIG. 8*j*).

g. Next, performing a conventional carotid stenting procedure. It should be noted that during stenting procedures where there is a risk of the formation of emboli; thus, the reverse flow means 1003 is activated in order to, as explained above, establish reverse blood flow into the body 1102 in order to capture any such emboli which may be generated during the procedure. Furthermore, in this stage, the third balloon 1007, distally to the blockage/occlusion, is independently inflated (either in the external carotid artery or in the internal carotid artery, depending where the blockage is; namely, if the blockage is in the external carotid artery, the third balloon 1007 is inflated in the external carotid artery, distally to the same), either by the introduction of a saline solution other fluid, thereby inflating the third balloon 1007. The location and amount of inflation can be provided to the surgeon by means of at least one marker visualized by imaging means (see FIGS. 8*k*, 8L and 8*m*).

h. Next, once the stent has been fully deployed the reverse flow means 1003 can be de-activated in order to terminate suction and thus the reversal of blood flow in the carotid artery.

i. As the vascular procedure is now completed, the first, second and third balloon 1005, 1006 and 1007 can then be (independently) deflated in order to allow normal blood flow to resume.

j. Next closure of the blood vessel is in order. If the sutures have been threaded by the aid of the closure device 100 at the beginning of the procedure, the next step is to secure the same. Alternatively, the sutures are now threaded and secured.

Figure 8N:
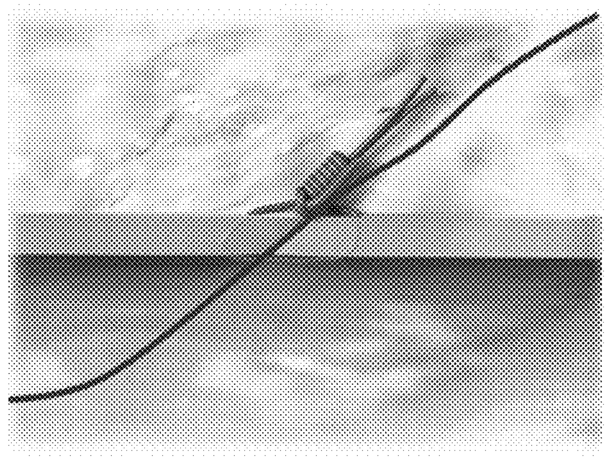

If the closure device is provided as a standalone device, it is now being introduced to the blood vessel (after the removal of the catheter 1000) and activated (see FIG. 8*n*).

k. Next, the catheter 1000 is fully withdrawn out from the patient.

l. Finally, the surgeon uses ultrasound to verify hemostasis and remove the guidewire.

It should be pointed out that either the withdrew blood is being thrown as biological disposal or it be can be re-introduced back to the vessel (depending or the amounts thereof and the medical requirements).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A closure device, comprising:

a proximal end and a distal end, interconnected by a main sheath; and at least two pre-shaped hollow tubes, each pre-shaped hollow tube comprising a proximal end positioned substantially at the proximal end of the closure device, and a distal end configured to be at least partially deployed from the distal end of the closure device into a blood vessel;

wherein upon deployment of the distal ends of the at least two pre-shaped hollow tubes into the blood vessel, the distal ends of the at least two pre-shaped hollow tubes are configured for engagement therebetween, to enable threading of a suture from a first tube of the at least two pre-shaped hollow tubes to a second tube of the at least two pre-shaped hollow tubes, wherein the distal end of one or more of the at least two pre-shaped hollow tubes comprises at least one mechanical mechanism configured to secure the engagement between the distal ends of the at least two pre-shaped hollow tubes and ensure alignment therebetween.

2. The closure device of claim 1, wherein each of the at least two pre-shaped hollow tubes comprises at least two configurations:

a first configuration, in which the pre-shaped hollow tube is confined within the closure device and has a shape substantially parallel to the main sheath of the closure device; and a second configuration, in which the pre-shaped hollow tube protrudes out of the distal end of the closure device and the distal end of the pre-shaped tube has a curved shape.

3. The closure device of claim 1, wherein the engagement of the at least two pre-shaped hollow tubes results in at least one continuous passage from the proximal end of the first tube of the at least two pre-shaped hollow tubes to the proximal end of the second tube of the at least two pre-shaped hollow tubes, through the engaged distal ends of the at least two pre-shaped hollow tubes.

4. The closure device of claim 3, wherein the at least one continuous passage is configured to automatically guide the suture from the proximal end of the first tube of the at least two pre-shaped hollow tubes to the proximal end of the second tube of the at least two pre-shaped hollow tubes, when the suture is inserted and advanced through the at least one continuous passage.

5. The closure device of claim 1, wherein the at least two pre-shaped hollow tubes are positioned externally to the main sheath of the closure device.

6. The closure device of claim 1, wherein the at least two pre-shaped hollow tubes are positioned internally within the main sheath of the closure device.

7. The closure device of claim 1, wherein the distal end of one or more of the at least two pre-shaped hollow tubes is cone-shaped.

8. The closure device of claim 1, comprising at least one alignment element configured to facilitate alignment between the at least two pre-shaped hollow tubes.

9. The closure device of claim 8, wherein the at least one alignment element comprises at least one groove configured to at least partially accommodate the distal ends of the two pre-shaped hollow tubes so as to facilitate alignment therebetween.

10. The closure device of claim 1, comprising at least one foot fixation element configured for deployment into the blood vessel and comprising at least two configurations:

a retracted configuration, in which the at least one foot fixation element is substantially parallel to the main sheath of the closure device; and a deployed configuration, in which the at least one foot fixation element is substantially parallel to a wall of the blood vessel.

11. The closure device of claim 10, wherein the at least one foot fixation element is configured to be positioned against an internal wall of the blood vessel and provide counter force to entry of the at least two pre-shaped hollow tubes into the blood vessel.

12. The closure device of claim 1, comprising at least one sensor configured to sense at least one of: (a) engagement between the distal ends of the at least two pre-shaped hollow tubes, (b) disengagement of the distal ends of the at least two pre-shaped hollow tubes from each other, (c) any combination thereof.

13. The closure device of claim 1, wherein the blood vessel is a carotid artery.

14. A transcarotid access system, comprising the closure device of claim 1; and at least one reversibly inflatable balloon.

15. The transcarotid access system of claim 14, wherein the at least one reversibly inflatable balloon comprises at least one marker configured to indicate at least one of: location within the blood vessel and an amount of inflation of the at least one balloon.

16. The transcarotid access system of claim 14, comprising at least one negative pressure generator configured to apply suction within the blood vessel to withdraw fluids therefrom.

17. The transcarotid access system of claim 14, comprising at least one filter configured to capture embolic particles.

18. A method for applying a suture to a blood vessel using a closure device comprising a proximal end and a distal end interconnected by a main sheath, and at least two pre-shaped hollow tubes each comprising a proximal end and a distal end, the method comprising:

deploying the distal ends of the at least two pre-shaped hollow tubes from the distal end of the closure device and into the blood vessel, until the distal ends of the at least two pre-shaped hollow tubes assume a curved shape and engagement is established therebetween; and threading a suture from the proximal end of a first tube of the at least two pre-shaped hollow tubes to the proximal end of a second tube of the at least two pre-shaped hollow tubes, through the engaged distal ends of the at least two pre-shaped hollow tubes.

19. The method of claim 18, wherein the closure device comprises at least one foot fixation element, and the method further comprises:

deploying the at least one foot fixation element from the distal end of the closure device; and positioning the at least one foot fixation element against an internal wall of the blood vessel to provide counter force to entry of the distal ends of the at least two pre-shaped hollow tubes into the blood vessel.

20. A closure device, comprising:

a proximal end and a distal end, interconnected by a main sheath;

at least two pre-shaped hollow tubes, each pre-shaped hollow tube comprising a proximal end positioned substantially at the proximal end of the closure device, and a distal end configured to be at least partially deployed from the distal end of the closure device into a blood vessel; and at least one alignment element configured to facilitate alignment between the at least two pre-shaped hollow tubes, the at least one alignment element comprising at least one groove configured to at least partially accommodate the distal ends of the at least two pre-shaped hollow tubes so as to facilitate alignment therebetween;

wherein upon deployment of the distal ends of the at least two pre-shaped hollow tubes into the blood vessel, the distal ends of the at least two pre-shaped hollow tubes are configured for engagement therebetween, to enable threading of a suture from a first tube of the at least two pre-shaped hollow tubes to a second tube of the at least two pre-shaped hollow tubes.

21. A closure device, comprising:

a proximal end and a distal end, interconnected by a main sheath;

at least two pre-shaped hollow tubes, each pre-shaped hollow tube comprising a proximal end positioned substantially at the proximal end of the closure device, and a distal end configured to be at least partially deployed from the distal end of the closure device into a blood vessel; and at least one foot fixation element configured for deployment into the blood vessel and comprising at least two configurations:

a retracted configuration, in which the at least one foot fixation element is substantially parallel to the main sheath of the closure device; and a deployed configuration, in which the at least one foot fixation element is configured to be substantially parallel to a wall of the blood vessel;

wherein upon deployment of the distal ends of the at least two pre-shaped hollow tubes into the blood vessel, the distal ends of the at least two pre-shaped hollow tubes are configured for engagement therebetween, to enable threading of a suture from a first tube of the at least two pre-shaped hollow tubes to a second tube of the at least two pre-shaped hollow tubes.

22. The closure device of claim 21, wherein the at least one foot fixation element is configured to be positioned against an internal wall of the blood vessel and provide counter force to entry of the at least two pre-shaped hollow tubes into the blood vessel.

23. A closure device, comprising:

a proximal end and a distal end, interconnected by a main sheath;

at least two pre-shaped hollow tubes, each pre-shaped hollow tube comprising a proximal end positioned substantially at the proximal end of the closure device, and a distal end configured to be at least partially deployed from the distal end of the closure device into a blood vessel; and at least one sensor configured to sense at least one of: (a) engagement between the distal ends of the at least two pre-shaped hollow tubes, (b) disengagement of the distal ends of the at least two pre-shaped hollow tubes from each other, (c) any combination thereof;

wherein upon deployment of the distal ends of the at least two pre-shaped hollow tubes into the blood vessel, the distal ends of the at least two pre-shaped hollow tubes are configured for engagement therebetween, to enable threading of a suture from a first tube of the at least two pre-shaped hollow tubes to a second tube of the at least two pre-shaped hollow tubes.

* * * * *